(12) United States Patent
Gizaw et al.

(10) Patent No.: US 9,993,418 B2
(45) Date of Patent: Jun. 12, 2018

(54) BENEFIT AGENT EMULSIONS AND CONSUMER PRODUCTS CONTAINING SUCH EMULSIONS

(71) Applicant: The Procter & Gamble Company, Cincinnati, OH (US)

(72) Inventors: Yonas Gizaw, West Chester, OH (US); Steven Daryl Smith, Fairfield, OH (US); Roy Jerome Harrington, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days. days.

(21) Appl. No.: 14/445,169

(22) Filed: Jul. 29, 2014

(65) Prior Publication Data

US 2015/0030557 A1    Jan. 29, 2015

Related U.S. Application Data

(60) Provisional application No. 61/859,748, filed on Jul. 29, 2013.

(51) Int. Cl.

| | |
|---|---|
| *A61Q 19/10* | (2006.01) |
| *A61K 8/898* | (2006.01) |
| *A61Q 5/02* | (2006.01) |
| *A61K 8/58* | (2006.01) |
| *A61Q 5/12* | (2006.01) |
| *A61K 8/69* | (2006.01) |
| *A61Q 17/00* | (2006.01) |
| *A61Q 19/00* | (2006.01) |
| *A61K 8/891* | (2006.01) |
| *A61K 8/893* | (2006.01) |
| *A61K 8/894* | (2006.01) |
| *A61K 8/06* | (2006.01) |
| *C11D 3/37* | (2006.01) |

(52) U.S. Cl.
CPC ............... *A61K 8/898* (2013.01); *A61K 8/06* (2013.01); *A61K 8/585* (2013.01); *A61K 8/69* (2013.01); *A61K 8/891* (2013.01); *A61K 8/893* (2013.01); *A61K 8/894* (2013.01); *A61Q 5/02* (2013.01); *A61Q 5/12* (2013.01); *A61Q 17/005* (2013.01); *A61Q 19/00* (2013.01); *A61Q 19/10* (2013.01); *C11D 3/3742* (2013.01)

(58) Field of Classification Search
None
See application file for complete search history.

(56) References Cited

U.S. PATENT DOCUMENTS

| | | |
|---|---|---|
| 3,560,543 A | 2/1971 | Plueddemann |
| 4,200,724 A | 4/1980 | Darms et al. |
| 4,293,397 A | 10/1981 | Sato |
| 4,533,714 A | 8/1985 | Sebag et al. |
| 4,833,225 A | 5/1989 | Schaefer et al. |
| 5,300,167 A | 4/1994 | Nohr et al. |
| 5,358,667 A | 10/1994 | Bergmann |
| 5,476,660 A | 12/1995 | Somasundaran |
| 5,659,001 A | 8/1997 | De La Croi Habimana et al. |
| 5,925,341 A | 7/1999 | Cervantes et al. |
| 6,093,240 A | 7/2000 | Matsumura et al. |
| 6,201,058 B1 | 3/2001 | Mahr et al. |
| 6,338,855 B1 | 1/2002 | Albacarys |
| 6,395,858 B1 | 5/2002 | Mack et al. |
| 6,491,838 B1 | 12/2002 | Standke et al. |
| 6,641,870 B2 | 11/2003 | Bartkowiak et al. |
| 6,833,344 B2 | 12/2004 | Boutique |
| 6,878,770 B2 | 4/2005 | Herzig |
| 6,903,061 B2 | 6/2005 | Masschelein |
| 7,118,057 B2 | 10/2006 | Hao |
| 7,217,777 B2 | 5/2007 | Lange et al. |
| 7,294,612 B2 | 11/2007 | Popplewell et al. |
| 7,514,091 B2 | 4/2009 | Restle et al. |
| 7,563,856 B2 | 7/2009 | Lange |
| 7,563,857 B2 | 7/2009 | Lange et al. |
| 7,871,972 B2 | 1/2011 | Sengupta |
| 7,888,306 B2 | 2/2011 | Sengupta |
| 8,158,572 B2 | 4/2012 | Schubert |
| 8,367,791 B2 | 2/2013 | Byrd et al. |
| 8,440,174 B2 | 5/2013 | Panandiker |
| 2003/0147842 A1 | 8/2003 | Restle et al. |
| 2004/0029981 A1 | 2/2004 | Herzig et al. |
| 2004/0048996 A1 | 3/2004 | Lange |
| 2004/0092424 A1 | 5/2004 | Boutique et al. |
| 2004/0092425 A1 | 5/2004 | Boutique et al. |
| 2004/0138400 A1 | 7/2004 | Lange |
| 2005/0009721 A1 | 1/2005 | Delplancke et al. |

(Continued)

FOREIGN PATENT DOCUMENTS

| | | |
|---|---|---|
| CN | 101956324 | 1/2011 |
| JO | H 07-053331 | 2/1995 |

(Continued)

OTHER PUBLICATIONS

U.S. Appl. No. 14/444,070, filed Jul. 28, 2014, Rajan Keshav Panandiker et al.
U.S. Appl. No. 14/444,038, filed Jul. 28, 2014, Rajan Keshav Panandiker et al.
International Search Report and Written Opinion dated Oct. 15, 2013, 9 pgs.
International Search Report and Written Opinion dated Oct. 30, 2013, 8 pgs.

(Continued)

*Primary Examiner* — Jyothsna A Venkat

(74) *Attorney, Agent, or Firm* — Jason J Camp

(57) ABSTRACT

Consumer product compositions providing enhanced hydrophobic benefit agent deposition. The benefit agent is provided as a benefit agent/deposition aid emulsion, where the benefit agent is physically adsorbed to the deposition aid before the emulsion is added to the balance of ingredients.

1 Claim, No Drawings

(56) References Cited

U.S. PATENT DOCUMENTS

| | | |
|---|---|---|
| 2005/0170994 A1* | 8/2005 | Casado-Dominguez ................. C08L 83/08 510/466 |
| 2006/0235181 A1 | 10/2006 | Lange et al. |
| 2007/0041929 A1 | 2/2007 | Torgerson |
| 2007/0041930 A1 | 2/2007 | Meder et al. |
| 2009/0142293 A1 | 6/2009 | Wagner et al. |
| 2010/0041583 A1* | 2/2010 | Ponder ................. C11D 3/3707 510/515 |
| 2010/0215604 A1 | 8/2010 | Van Flordrop et al. |
| 2010/0247472 A1 | 9/2010 | Sau |
| 2011/0135588 A1 | 6/2011 | Uehara |
| 2011/0243878 A1* | 10/2011 | Panandiker .......... C08G 77/388 424/78.03 |
| 2012/0037040 A1 | 2/2012 | Standke et al. |
| 2012/0276175 A1 | 11/2012 | Dihora |
| 2014/0020188 A1* | 1/2014 | Gizaw et al. ...................... 8/137 |
| 2014/0024780 A1* | 1/2014 | Benlahmar et al. .......... 525/102 |
| 2014/0030206 A1 | 1/2014 | Smith et al. |
| 2014/0128521 A1 | 5/2014 | Sekiya et al. |
| 2014/0206805 A1 | 7/2014 | Sekiya et al. |
| 2015/0225313 A1 | 8/2015 | Schmidt et al. |
| 2015/0307417 A1 | 10/2015 | Schmidt et al. |

FOREIGN PATENT DOCUMENTS

| | | |
|---|---|---|
| JP | H 07-053330 | 2/1995 |
| JP | H 07-053332 | 2/1995 |
| JP | 2002308723 A | 10/2002 |
| JP | A-2002-308991 | 10/2002 |
| JP | H 05-320349 | 10/2013 |
| WO | WO9811870 A1 | 3/1998 |
| WO | WO9932539 A1 | 7/1999 |
| WO | WO 2000/71806 | 11/2000 |
| WO | WO 2002/018528 | 3/2002 |
| WO | WO 2004/041987 | 5/2004 |
| WO | WO 2005/009721 A1 | 2/2005 |
| WO | WO 2011/123727 A | 10/2011 |
| WO | WO 2014/018985 | 1/2014 |

OTHER PUBLICATIONS

International Search Report and Written Opinion dated Oct. 30, 2013, 9 pgs.

International Search Report and Written Opinion dated Oct. 18, 2013, 9 pgs.

* cited by examiner

BENEFIT AGENT EMULSIONS AND CONSUMER PRODUCTS CONTAINING SUCH EMULSIONS

FIELD OF THE INVENTION

The present invention relates to benefit agent emulsions and consumer products compositions containing such emulsions. The emulsions and products facilitate increased deposition and retention of benefit agents contained therein onto a substrate.

BACKGROUND OF THE INVENTION

Many consumer products contain benefit agents intended for delivery and deposition onto a negatively charged target surface (e.g., fabric, skin, or hair). These products can provide consumer-desired benefits such as softness, hand, anti-wrinkle, hair conditioning, frizz control, skin moisturization, and color protection. Difficulties frequently arise in achieving effective deposition of benefit agents onto these surfaces when the benefit agent is delivered via rinse-off consumer product compositions, especially when those compositions are cleansing products.

Cleansing products such as shampoos, bodywashes, liquid soaps, and laundry detergents typically contain an excess of anionic surfactant. This makes deposition and retention of hydrophobic benefit agents onto an anionic target surface especially difficult. Various cationic polymers have been proposed as deposition aids for such compositions, but their performance is not always wholly satisfactory. For instance, anionic surfactants can interfere with cationic deposition aid performance by adsorbing onto the deposition aid, as well as by forming complexes that lead to poor shelf stability and loss of cleaning efficacy (e.g., due to flocculation and precipitation). In addition to poor benefit agent delivery, this leads to non-cost-effective use and waste of materials.

Furthermore, while increasing the deposition of the desired benefit agent, deposition aids unfortunately can also increase the deposition of undesired materials such as soil and/or alter the nature of the desired benefit agent. When the deposition aid deposits soil, the whiteness, feel, appearance, and/or cleaning benefits are decreased. When the nature of the desired benefit agent is negatively impacted by the deposition aid, the benefit agent's effectiveness may be decreased and/or the consumer experience arising from the benefit agent's use may be altered in a negative manner.

Deposition aids undergo hydrophobic and/or electrostatic interactions with not only benefit agents, but also other materials, such as soils, to form particulates that have an affinity for consumer relevant substrates such as hair, skin, fabrics, and/or hard surfaces. Such interactions may be particularly pronounced in the presence of surfactants. Thus, there is a need to provide a deposition aid that achieves effective deposition of benefit agents but not of undesired substances.

Many cationic polymers disclosed in the art are not wholly satisfactory for use as deposition aids in consumer product compositions. For example, the material described by Ono (WO 99/32539) comprises end groups having heteroatoms such as oxygen, nitrogen, sulfur, or halogens. These functionalized end groups can lead to undesirable reactions that pose stability issues for compositions comprising these materials. For instance, Ono's silicones can react further through these end groups, leading to further condensation/polymerization of the silicones in the compositions during storage.

Also known in the art are quaternized silicones that include alkylene oxide units, such as U.S. Pat. No. 6,903,061 to Masschelein. The quaternized silicones described by Masschelein tend to be too water soluble, and thus have a reduced capacity as deposition aids, since these materials tend to partition into water at a higher than desired level. Further, when these materials are used as the deposition active, they have an undesirable feel because of their high permeability to water and water vapor. In addition, because of their water solubility, these materials can be difficult to formulate reproducibly. Further, Masschelein discloses materials having only one quaternized nitrogenous group per side of the molecule. This can limit the desired degree of functionality in a silicone material. It would desirable to have a material that provides greater flexibility via the level of quaternization. Similarly, the ethoxylated quaternized silicone materials disclosed by Boutique in U.S. Pat. No. 6,833,344 suffer from many of the same inadequecies of those described by Masschelein.

In an effort to prevent incompatibilities among consumer product composition ingredients, the prior art discloses hydrophobic benefit agents encapsulated within a wall comprising hydrophilic, water-soluble polymers, such as those disclosed in U.S. Pat. No. 7,118,057, U.S. Pat. No. 7,294,612, and WO 98/11870. The encapsulated benefit agent is mixed into a cleansing/wash-off product composition comprising surfactant. While encapsulation may prevent undesired reactions between ingredients, it can also limit the amount of benefit agent available for surface treatment. Even if the benefit agent capsule adequately deposits onto the substrate, the level of benefit agent available for surface treatment can be limited to that amount which can diffuse through the capsule wall and/or leak due to breakage of the capsule.

Thus there remains a need for additional consumer product cleansing compositions that can adequately deposit hydrophobic benefit agents onto a negatively charged substrate without suffering from the aforementioned deficiencies.

SUMMARY OF THE INVENTION

The present invention attempts to solve one or more of the aforementioned needs by providing, in one aspect, consumer product compositions comprising an inventive benefit agent emulsion. The emulsions and products disclosed herein can deliver a desired level of benefit agent deposition. Further, once deposited on the substrate, the benefit agents are available in a physical form that is suitable for providing the desired end-use properties, such as hair-conditioning, fabric softening, and skin-moisturizing. This enhanced performance is attributed to the specific additive-form in which the benefit agents are incorporated into the consumer product compositions, as well as to the inventive deposition aid disclosed herein. According to the present invention, the benefit agent is provided as a benefit agent/deposition aid emulsion, where the benefit agent is physically blended (e.g., adsorbed) with the deposition-aid before addition to the other consumer product composition ingredients.

DETAILED DESCRIPTION OF THE INVENTION

In one aspect, the present invention provides a benefit agent emulsion comprising a benefit agent and a cationic deposition aid which may be adsorbed to the surface of the benefit agent. In one aspect, the benefit agent is hydrophobic. In a particular aspect, the emulsion is substantially free of surfactant, although the consumer product composition may contain surfactant.

In another aspect, the invention provides a method for making a cleansing or surface-conditioning consumer product composition. The method comprises: (a) providing the benefit agent emulsion; (b) providing an auxiliary composition; and (c) combining said emulsion and said auxiliary composition to form the consumer product composition. The auxiliary composition comprises the balance of ingredients which, in combination with the emulsion, form the final consumer product composition. The auxiliary composition can comprise one or more separate compositions, which can be combined with the emulsion either separately or together to form the final consumer product. In particular embodiments, the auxiliary composition comprises a solvent (e.g., a hydrophilic solvent such as water) and/or surfactant, as well as any other desired ingredients.

Adsorption between the benefit agent (e.g., hydrophobic benefit agent) and the cationic deposition aid is achieved in the emulsion composition prior to its addition to the auxiliary composition. Pre-adsorbing the deposition aid to the benefit agent promotes deposition efficiency and dispersion stability (i.e., against flocculation and coalescence) of the emulsion components when the emulsion is dispersed in aqueous or other hydrophilic solutions, especially those comprising surfactant.

In particular embodiments, the benefit agent can be encapsulated within a capsule-like enclosure; in other embodiments, the benefit agent is not encapsulated. Encapsulation can limit the amount of benefit agent available for surface treatment, yet can also prevent adverse interactions between the benefit agent and other ingredients. Thus, the desirability of encapsulation will depend upon, for example, the level of benefit agent that can diffuse through the capsule wall or leak due to breakage, versus the consequences of adverse ingredient interactions.

In one aspect, the emulsion is in the form of an oil-in-water emulsion, wherein the emulsion comprises at least one hydrophobic liquid, which can be the benefit agent or can be in addition to the benefit agent. The hydrophobic benefit agent can be homogenously dispersed in the hydrophobic liquid. For instance, in one embodiment the emulsion is in the form of an emulsified oil droplet in an oil-in-water emulsion, wherein the deposition-aid serves as an emulsifier for emulsifying the benefit agent phase in a water phase, prior to mixing the oil-in-water emulsion (i.e., emulsion) with the auxiliary composition.

In one embodiment, the surfactant can be selected from the group consisting of anionic, non-ionic, zwitterionic, cationic, amphoteric, and mixtures thereof. In particular embodiments, the surfactant comprises anionic surfactant.

In one embodiment, the hydrophobic benefit agent is selected from the group consisting of silicone, a vinyl polymer, a polyether, a material comprising a hydrocarbon wax, a hydrocarbon liquid, a fluid sugar polyester, a fluid sugar polyether, and mixtures thereof.

In another aspect, the invention provides a method of depositing a benefit agent onto a substrate comprising contacting the substrate with the emulsion, which can be delivered in the form of the consumer product composition. In another aspect, the invention provides a method of providing hair conditioning, skin moisturizing, fabric softening, or a fabric anti-wrinkle property comprising contacting the finished consumer product composition with a substrate selected from the group consisting of hair, skin, and fabric.

Consumer product compositions described herein are suitable for use as cleansing and/or surface-conditioning products like shampoos, body-washes, liquid soaps, laundry detergents, and fabric softeners, which allow substantive deposition and retention on the hair, skin, and fabric of one or more benefit agents, desirably hydrophobic benefit agents, contained therein.

In one aspect, the present invention provides a benefit agent emulsion comprising a benefit agent and a cationic deposition aid, wherein said cationic deposition aid is a pendant organopolysiloxane having the formula:

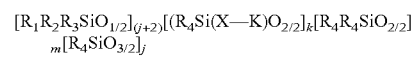

wherein:
j is an integer from 0 to about 98; in one aspect j is an integer from 0 to about 48; in one aspect, j is 0;
k is an integer from 1 to about 200, in one aspect k is an integer from 1 to about 50;
m is an integer from 4 to about 5,000; in one aspect m is an integer from about 10 to about 4,000; in another aspect m is an integer from about 50 to about 2,000;
$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy and X—K;
each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy; for each X—K X comprises a divalent alkylene radical comprising 2-12 carbon atoms, in one aspect, each divalent alkylene radical is independently selected from the group consisting of —$(CH_2)_s$— wherein s is an integer from 2 to 8, or an integer from 2 to 4; and each K is selected independently from the group consisting of:

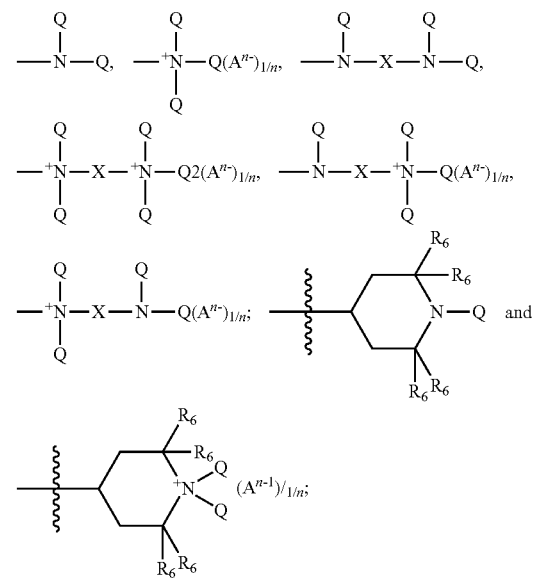

each Q is independently a H or a $C_1$-$C_{32}$, linear or branched, substituted or unsubstituted hydrocarbon, with the proviso that when K is a quat, Q cannot be an amide, imine, or urea moiety and if Q is an amide, imine, or urea moiety, then any additional Q bonded to the same nitrogen as said amide, imine, or urea moiety must be H or a $C_1$-$C_6$ alkyl, in one aspect, said additional Q is H; X is defined as above;

for K $A^{n-}$ is a suitable charge balancing anion. In one aspect $A^{n-}$ is selected from the group consisting of $Cl^-$, $Br^-$, $I^-$, methylsulfate, toluene sulfonate, carboxylate and phosphate;

for cationically charged K, $A^{n-}$ is a suitable charge balancing anion, in one aspect $A^{n-}$ is selected from the group consisting of $Cl^-$, $Br^-$, $I^-$, methylsulfate, toluene sulfonate, carboxylate and phosphate;

wherein the pendant organopolysiloxane and the benefit agent are identical or different relative to each other.

The pendant organopolysiloxane can have a molecular weight from about 1000 Daltons to about 1,000,000 Daltons; from about 10,000 Daltons to about 100,000 Daltons; or from about 15,000 Daltons to about 50,000 Daltons.

The ratio of benefit agent to organopolysiloxane can be from 1000:1 to 1:1; or from 500:1 to 5:1; or from 250:1 to 5:1; or from 100:1 to 5:1; or from 100:1 to 10:1, all by weight. In a particular embodiment, the ratio of benefit agent to organopolysiloxane is from 40:1 to 20:1, all by weight.

In one embodiment, the consumer product composition comprises a silicone benefit agent material selected from the group consisting of a polydimethylsiloxane, an aminosilicone, a cationic silicone, a silicone polyether, a cyclic silicone, a silicone resin, a fluorinated silicone and mixtures thereof. In some embodiments, a) said polydimethylsiloxane has a viscosity from 10 centistokes (cSt) to 2,000,000 cSt; from 50 cSt to 1,000,000 cSt; from 500 cSt to 100,000 cSt; or from 750 cSt to 1000 cSt; b) said aminosilicone has a viscosity from 100 cSt to 300,000 cSt; from 500 cSt to 200,000 cSt; from 750 cSt to 50,000 cSt; or from 1000 cSt to 5000 cSt; c) said cationic silicone has a viscosity from 100 cSt to 1,000,000 cSt; from 500 cSt to 500,000 cSt; from 750 cSt to 50,000 cSt; or from 1000 cSt to 5000 cSt; d) said silicone polyether has a viscosity from 100 cSt to 1,000,000 cSt; from 500 cSt to 500,000 cSt; from 750 cSt to 50,000 cSt; or from 1000 cSt to 5000 cSt; e) said cyclic silicone has a viscosity from 10 cSt to 10,000 cSt; from 50 cSt to 5,000 cSt; from 100 cSt to 2,000 cSt; or from 200 cSt to 1000 cSt; 0 said silicone resin has a viscosity from 10 cSt to 10,000 cSt; from 50 cSt to 5,000 cSt; from 100 cSt to 2,000 cSt; or from 200 cSt to 1000 cSt; and g) said fluorinated silicone has a viscosity from 100 cSt to 300,000 cSt; from 500 cSt to 200,000 cSt; from 750 cSt to 50,000 cSt; or from 1000 cSt to 5000 cSt.

In some embodiments, the silicone benefit agent material has the structure:

$$[R_1R_2R_3SiO_{1/2}]_{(j+2)}[(R_4Si(X-Z)O_{2/2}]_k[R_4R_4SiO_{2/2}]_m[R_4SiO_{3/2}]_j$$

wherein:
j is an integer from 0 to about 98; in one aspect j is an integer from 0 to about 48; in one aspect, j is 0;
k is an integer from 1 to about 200; in one aspect, k is an integer from 1 to about 50;
m is an integer from 4 to about 5,000; in one aspect m is an integer from about 10 to about 4,000; in another aspect m is an integer from about 50 to about 2,000;
$R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy and X—Z;
each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy;
for each X—Z,
X comprises a divalent alkylene radical comprising 2-12 carbon atoms; and
at least one Z in the said silicone benefit agent material is selected from the group consisting of $R_5$;

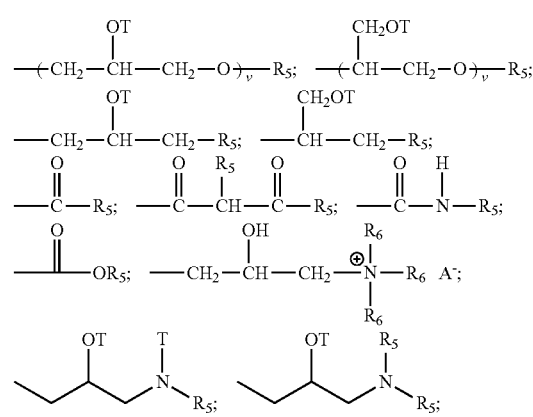

each additional Z in said silicone benefit agent material is independently selected from the group comprising of H, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $R_5$,

each $R_5$ is independently selected from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl or $C_6$-$C_{32}$ alkylaryl, or $C_6$-$C_{32}$ substituted alkylaryl, —(CHR_6—CHR_6—O—)_w—CHR_6—CHR_6-L and a siloxyl residue;
w is an integer from 0 to about 500, in one aspect w is an integer from 0 to about 200, one aspect w is an integer from 0 to about 50;
each $R_6$ is independently selected from H or a $C_1$-$C_{18}$ alkyl;
wherein each L is independently selected from —O—C(O)—$R_7$ or —O—$R_7$;

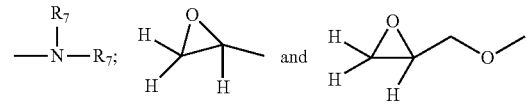

each $R_7$ is independently selected from the group consisting of H; $C_1$-$C_{32}$ alkyl; $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, and $C_6$-$C_{32}$ substituted aryl, and a siloxyl residue;
each T is independently selected from H;

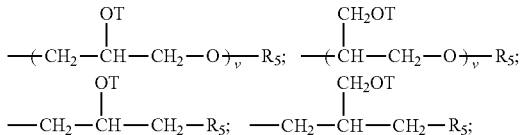

wherein each v in said silicone benefit agent material is an integer from 1 to about 10, in one aspect, v is an integer from 1 to about 5 and the sum of all v indices in each Z in the said silicone benefit agent material is an integer from 1 to about 30 or from 1 to about 20 or from 1 to about 10, with the proviso that the total moieties T in a molecule does not exceed 6.

Some of the consumer product compositions comprise from 0.1% to 25%, or from 0.1% to 20%, or from 0.1% to 15%, or from 0.1% to 10%, or from 0.1% to 5%, or from 0.1% to 1% or from 0.25% to 25%, or from 0.5% to 20%, or from 1% to 15%, of the benefit agent emulsion by weight.

The consumer product composition can be in any suitable form. In one embodiment, the consumer product composition is in the form selected from the group consisting of shampoo, conditioners, body wash, detergent, fabric enhancers, antimicrobial wash, and hard surface cleaner. The consumer product composition can comprise a hydrophobic benefit agent, for instance one selected from the group consisting of silicone, fragrance, emollient, antimicrobial agent, sunscreen, lipid, oil, hydrocarbon, wax, hydrophobically-modified pigment, inorganic compound, and mixtures thereof.

The present invention also provides a consumer product composition comprising the inventive emulsion, and an auxiliary composition. The consumer product composition can comprise surfactant selected from the group consisting of cationic, anionic, amphoteric, zwitterionic, non-ionic, and combinations thereof. In some embodiments, the consumer product comprises a benefit agent selected from the group consisting of a silicone, a vinyl polymer, a polyether, a material comprising a hydrocarbon wax, a hydrocarbon liquid, a fluid sugar polyester, a fluid sugar polyether, and mixtures thereof. The consumer product composition can additionally comprise a second benefit agent selected from the group consisting of clays, metal oxides, silicones, and microcapsules.

The present invention also provides a method of providing hair conditioning, skin moisturizing, fabric softening, or a fabric anti-wrinkle property, comprising contacting a substrate selected from the group consisting of hair, skin, and fabric with the inventive emulsion or consumer product comprising said emulsion. It also provides a method of depositing a hydrophobic benefit agent onto a substrate, comprising contacting said substrate with the inventive emulsion or consumer product comprising said emulsion.

Features and benefits of the various embodiments of the present invention will become apparent from the following description, which includes examples of specific embodiments intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

I. Definitions

As used herein "consumer product" means baby care, personal care, fabric & home care, family care (e.g., facial tissues, paper towels), feminine care, health care, beauty care and like products generally intended to be used or consumed in the form in which they are sold. Such products include but are not limited to diapers, bibs, wipes; products for and/or methods relating to treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for and/or methods relating to treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, and other cleaning for consumer or institutional use; products and/or methods relating to bath tissue, facial tissue, paper handkerchiefs, and/or paper towels; tampons, feminine napkins; products and/or methods relating to oral care including toothpastes, tooth gels, tooth rinses, denture adhesives, and tooth whitening.

As used herein, the term "cleansing and/or treatment composition" is a subset of consumer products that includes, unless otherwise indicated, personal care, fabric care, and home care products. Such products include, but are not limited to, products for treating hair (human, dog, and/or cat), including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products, products for treating fabrics, hard surfaces and any other surfaces in the area of fabric and home care, including: air care including air fresheners and scent delivery systems, car care, dishwashing, fabric conditioning (including softening and/or freshening), laundry detergency, laundry and rinse additive and/or care, hard surface cleaning and/or treatment including floor and toilet bowl cleaners, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, dentifrice, car or carpet shampoos, bathroom cleaners including toilet bowl cleaners; hair shampoos and hair-rinses; shower gels, fine fragrances and foam baths and metal cleaners; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists all for consumer or/and institutional use; and/or methods relating to oral care including toothpastes, tooth gels, tooth rinses, denture adhesives, tooth whitening. The care agents can advantageously be used in household polishes and cleaners for floors and countertops to provide benefits such as enhanced shine. Care agents in fabric softeners can help preserve "newness" because of their softening properties, and those having elasticity can help smooth out wrinkles. The care agents can also enhance shoe cleaning and polishing products.

As used herein, the term "personal care cleansing and/or treatment composition" is a subset of cleaning and treatment compositions that includes, unless otherwise indicated, products for treating hair, including, bleaching, coloring, dyeing, conditioning, shampooing, styling; deodorants and antiperspirants; personal cleansing; cosmetics; skin care including application of creams, lotions, and other topically applied products for consumer use including fine fragrances; and shaving products; liquid cleaning and disinfecting agents including antibacterial hand-wash types, cleaning bars, mouthwashes, denture cleaners, and dentifrice cleaners; hair shampoos and hair-rinses; shower gels, fine fragrances, and foam baths; substrate-laden products such as dry and wetted wipes and pads, nonwoven substrates, and sponges; as well as sprays and mists all for consumer or/and institutional use; and/or methods relating to oral care including toothpastes, tooth gels, tooth rinses, denture adhesives, and tooth whitening.

As used herein, the term "fabric and/or hard surface cleansing and/or treatment composition" is a subset of cleaning and treatment compositions that includes, unless otherwise indicated, granular or powder-form all-purpose or "heavy-duty" washing agents, especially cleaning detergents; liquid, gel or paste-form all-purpose washing agents, especially the so-called heavy-duty liquid types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, car or carpet shampoos, bathroom cleaners including toilet bowl cleaners; and metal cleaners, fabric conditioning products including softening and/or freshening that may be in liquid, solid and/or dryer sheet form; as well as cleaning auxiliaries such as bleach additives and "stain-stick" or pre-treat types, substrate-laden products such as dryer added sheets, dry and wetted wipes and pads, nonwoven substrates, and sponges; as well as sprays and mists. All of such products, as applicable, may be in standard, concentrated or even highly concentrated form even to the extent that such products may in certain aspects be non-aqueous.

As used herein, articles such as "a" and "an" are understood to mean one or more of what is claimed or described.

As used herein, the terms "include", "contain", and "have" are non-limiting and do not exclude other components or features beyond those expressly identified in the description or claims.

As used herein, the terms "treatment agent", "benefit agent", "active", "active agent", and/or "care agent" and the like are used interchangeably to mean materials that can impart desirable aesthetic and/or functional properties (e.g., conditioning benefits such as softening or freshening) to a substrate.

As used herein, the terms "conditioning agent" and "conditioning aid" are used interchangeably to refer to a material that delivers desirable conditioning effects (e.g., benefits such as softening or freshening) to a substrate. Conditioning agents are a type of treatment agent.

As used herein, the term "conditioning polymer" means a polymer that delivers desirable conditioning effects (e.g., softening or freshening) to a substrate.

As used herein, the term "substrate" is synonymous and used interchangeably with the terms "situs" and "surface". Non-limiting examples of substrates include paper products, fabrics, garments, hard surfaces, hair, and skin.

As used herein, "targeted substrate" means a substrate, or the relevant portion of a substrate, upon which deposition is intended.

As used herein, a "deposition aid" is a material that assists another material (e.g., a benefit agent) to deposit (e.g., adhere) to a targeted substrate. The term "deposition aid" is broad enough to encompass both polymeric deposition aids (i.e. "deposition polymer") and non-polymeric deposition aids.

As used herein, "adjunct" means an optional material that can be added to a composition to complement the aesthetic and/or functional properties of the composition.

As used herein, "auxiliary composition" refers to one or more compositions that when combined with a benefit agent emulsion of the present invention, form a consumer product composition. The auxiliary composition may be in the form of one or more ingredients or ingredient combinations.

As used herein, "carrier" means an optional material, including but not limited to a solid or fluid, that can be combined with a benefit agent (e.g., conditioning polymers) to facilitate delivery and/or use of the benefit agent.

As used herein, the term "solid" includes granular, powder, bar and tablet product forms.

As used herein, the term "fluid" includes liquid, gel, paste and gas product forms including unitized-dose forms that generally include a fluid composition enclosed in a pouch or other delivery vehicle.

As used herein, the term "particle" includes solid and semi-solid particles, as well as emulsion droplets.

Unless otherwise indicated, all percentages and ratios herein are by weight.

All percentages and ratios are calculated based on the weight of the total composition unless otherwise indicated.

Unless specified otherwise, all molecular weights are given in Daltons.

Unless otherwise indicated, all molecular weights are weight average molecular weights as determined by size exclusion chromatography using a MALS detector (SEC-MALS), as is commonly known by those skilled in the art. A MALS detector (Multi-Angle Light Scattering Detector, such as those manufactured by Malvern Instruments Ltd., Malvern, UK) determines absolute molecular weight, rather than relative molecular weight (i.e., determined relative to a standard).

Unless otherwise noted, all component (i.e., ingredient) or composition levels are in reference to the active portion of that component or composition, and are exclusive of impurities, for example, residual solvents or by-products, which may be present in commercially available sources of such components or compositions.

The term "charge density", as used herein, refers to the ratio of the number of positive charges on a monomeric unit of which a polymer is comprised, to the molecular weight of said monomeric unit. The charge density multiplied by the polymer molecular weight determines the number of positively charged sites on a given polymer chain. Charge density can also be expressed in the form of an equation as:

$$\text{charge density} = $$

$$\frac{(\text{moles of Nitrogen})(\text{charge per Nitrogen})}{(\text{moles of polymer})(\text{molecular weight of the polymer})} \times 100$$

As used herein, the term "hydrocarbon polymer radical" means a polymeric radical comprising only carbon and hydrogen.

As used herein, "ethylene moiety" means a divalent $CH_2CH_2$ moiety.

As used herein, the term "siloxyl residue" means a polydialkylsiloxane moiety.

As used herein, the nomenclature $SiO_{n/2}$ represents the ratio of oxygen and silicon atoms. For example, $SiO_{1/2}$ means that, on average, one oxygen atom is shared between two silicon atoms. Likewise $SiO_{2/2}$ means that, on average, two oxygen atoms are shared between two silicon atoms and $SiO_{3/2}$ means that, on average, three oxygen atoms are shared between two silicon atoms.

As used herein, the terms "substantially no", "substantially free of", and/or "substantially free from" mean that the indicated material is at the very minimum not deliberately added to the composition to form part of it, or, preferably, is not present at analytically detectable levels. It is meant to include compositions whereby the indicated material is present only as an impurity in one of the other materials deliberately included.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

II. Consumer Product Composition Comprising Benefit Agent Emulsion

Applicants observe that when making the consumer product, the order in which the ingredients are mixed can greatly affect the final composition's deposition performance. Although not wishing to be bound by theory, it is believed that in order for a cationic deposition aid to function most efficiently, it must first adsorb onto the benefit agent. Emulsifying the cationic deposition aid with the hydrophobic benefit agent allows the deposition aid to pre-adsorb onto the benefit agent before these ingredients are incorporated into the balance of ingredients in the auxiliary composition which can contain anionic surfactant.

Given that most cleansing products contain relatively high amounts of anionic surfactants but relatively low levels of benefit agents and deposition aid, binding of the deposition aid onto the benefit agent may be problematic if these ingredients are added separately to compositions that may include ingredients such as anionic surfactants. For example, factors such as high concentration of anionic surfactants and strong interaction (electrostatic) between an anionic surfactant and a cationic deposition polymer are likely to favor association between the anionic surfactant and the cationic deposition polymer over that between the weakly interacting, low-level cationic polymer and hydrophobic benefit agent.

Further, since the amount of anionic surfactant likely to adsorb on the hydrophobic benefit agent would be much smaller than the amount of the surfactant remaining dissolved (i.e., non-adsorbed) in the solution-phase, the cationic deposition polymer is most likely to associate/form complexes (i.e., anionic complexes in anionic surfactant-rich solutions) with the dissolved surfactant molecules rather than with any surfactant molecules pre-adsorbed on the benefit agent. Being present at a much higher concentration than any cationic polymer-anionic surfactant complex that could potentially form, the anionic surfactant may adsorb to the hydrophobic benefit agent far more easily than to the polymer-surfactant complex, such that the cationic deposition polymer may not be able to adsorb to the benefit agent to any considerable extent. Thus, when these two materials are added separately as ingredients to anionic surfactant-rich cleansing product compositions, the hydrophobic benefit agent may simply dissolve in the surfactant-rich solution.

It is often theorized in the art that association between the cationic deposition polymer and the hydrophobic benefit agent is achieved only when the cleansing products get heavily diluted during the course of the rinsing process. However, in this scenario, large portions of the added deposition polymer and the benefit agent would be rinsed off before the optimum dilution level is reached.

In order to efficiently deliver the end-use benefits (e.g., hair-conditioning, fabric-softening, fragrance-extension) of the hydrophobic benefit agents, the benefit agent must not only substantially deposit on the treated substrate, but it must also be available in a physical form that is suitable for providing the desired end-use benefit. For example, deposition of a hydrophobic substance such as silicone on the hair or on a fabric causes hydrophobic-modification of the hair or the fabric surface, which in turn leads to effects that manifest as hair-conditioning or fabric-softening benefits.

In one aspect, the present invention provides a benefit agent emulsion comprising a benefit agent and a cationic deposition aid bonded to the surface of the benefit agent. In one aspect, the benefit agent is hydrophobic. In a particular aspect, the emulsion is substantially free of surfactant.

In another aspect, the invention provides a method for making a cleansing or surface-conditioning consumer product composition. The method comprises: (a) providing the benefit agent emulsion; (b) providing an auxiliary composition; and (c) combining said emulsion and said auxiliary composition to form the consumer product composition. The auxiliary composition comprises the balance of ingredients which, in combination with the emulsion, form the final consumer product composition. The auxiliary composition can comprise one or more separate compositions, which can be combined with the emulsion either separately or together to form the final consumer product. In particular embodiments, the auxiliary composition comprises a solvent (e.g., a hydrophilic solvent such as water) and/or surfactant, as well as any other desired ingredients.

Adsorption between the benefit agent (e.g., hydrophobic benefit agent) and the cationic deposition aid is achieved in the emulsion composition prior to its addition to the auxiliary composition. Pre-adsorbing the deposition aid to the benefit agent promotes deposition efficiency and dispersion stability (i.e., against flocculation and coalescence) of the emulsion components when the emulsion is dispersed in aqueous or other hydrophilic solutions, especially those comprising surfactant.

In particular embodiments, the benefit agent can be encapsulated within a capsule-like enclosure; in other embodiments, the benefit agent is not encapsulated. Encapsulation can limit the amount of benefit agent available for surface treatment, yet can also prevent adverse interactions between the benefit agent and other ingredients. Thus, the desirability of encapsulation will depend upon, for example, the level of benefit agent that can diffuse through the capsule wall or leak due to breakage, versus the consequences of adverse ingredient interactions.

In one aspect, the emulsion is in the form of an oil-in-water emulsion, wherein the emulsion comprises at least one hydrophobic liquid, which can be the benefit agent or can be in addition to the benefit agent. The hydrophobic benefit agent can be homogenously dispersed in the hydrophobic liquid. For instance, in one embodiment the emulsion is in the form of an emulsified oil droplet in an oil-in-water emulsion, wherein the deposition-aid serves as an emulsifier for emulsifying the benefit agent phase in a water phase, prior to mixing the oil-in-water emulsion (i.e., emulsion) with the auxiliary composition.

In one embodiment, the surfactant can be selected from the group consisting of anionic, non-ionic, zwitterionic, cationic, amphoteric, and mixtures thereof. In particular embodiments, the surfactant comprises anionic surfactant.

In one embodiment, the hydrophobic benefit agent is selected from the group consisting of silicone, fragrance, emollient, antimicrobial agent, sunscreen, lipid, oil, hydrocarbon, wax, hydrophobically-modified pigment, inorganic compound, and mixtures thereof.

In another aspect, the invention provides a method of depositing a benefit agent onto a substrate comprising contacting the substrate with the emulsion, which can be delivered in the form of the consumer product composition. In another aspect, the invention provides a method of providing hair conditioning, skin moisturizing, fabric softening, or a fabric anti-wrinkle property comprising contacting the finished consumer product composition with a substrate selected from the group consisting of hair, skin, and fabric.

Consumer product compositions described herein are suitable for use as cleansing and/or surface-conditioning products like shampoos, body-washes, liquid soaps, laundry detergents, and fabric softeners, which allow substantive deposition and retention on the hair, skin, and fabric of one or more benefit agents, desirably hydrophobic benefit agents, contained therein.

In one embodiment, the hydrophobic benefit agent and the cationic polymer deposition aid are simply mixed together using techniques known in the art in order to form the emulsion of the present invention. Optionally, hydrophilic solvent and/or other ingredients that do not interfere with the adsorption of the deposition aid to the hydrophobic benefit agent can also be present in the emulsion.

The hydrophobic benefit agent can be any suitable agent for the desired end-use benefit. For example, the benefit agent can be selected from the group consisting of silicone, fragrance, emollient, antimicrobial agent, sunscreen, lipid, oil, hydrocarbon, wax, hydrophobically-modified pigment, inorganic compound, and mixtures thereof.

In one embodiment, the hydrophobic benefit agent and/or the emulsion is prepared in the form of an oil-in-water (O/W) emulsion. In a particular embodiment, the hydrophobic benefit agent of the emulsion is homogenously dispersed in a hydrophobic liquid. In another embodiment, the hydrophobic benefit agent itself serves as the hydrophobic liquid.

The cationic polymer deposition aid can serve as the emulsifier for emulsifying the benefit agent phase in a hydrophilic phase, such as a water phase. Alternatively, an alternate emulsifier can be used to emulsify the hydrophobic benefit agent with the hydrophilic (e.g., water) phase. For example, in some embodiments the benefit agent emulsifier can comprise a water-insoluble particulate material comprising a surface-active or a water-insoluble anionic polymer. In one embodiment, an anionic polymer is included in the range of 0.1% to 5% by weight, based on the weight of the oil-phase of the oil-in-water emulsion. Alternatively in some embodiments, the emulsifier can comprise a water-soluble, high molecular weight cationic polymer that is insoluble in anionic surfactant solutions. High-shear mixing methods as known in the art can be used to form the emulsions contemplated herein.

Optional ingredients that do not adversely affect the adsorption of the hydrophobic benefit agent (or the emulsified hydrophobic benefit agent) to the cationic polymer deposition aid can also be included in the emulsions and/or emulsion, depending upon the particular attributes desired in the end-use consumer product.

In order to form the finished consumer product composition, the emulsion is combined with the auxiliary composition comprising surfactant. In one embodiment, the consumer product compositions comprise from 0.5% to 95% by weight of surfactant. In some embodiments, the surfactant comprises anionic surfactant. Desired optional ingredients can be included in the auxiliary composition, the emulsion if they are compatible therewith, or can be added separately to the consumer product composition. Mixing methods as known in the art can be used to form the consumer product compositions herein.

The consumer product composition can be in any desired form. For instance, the composition form can be selected from the group consisting of shampoo, bodywash, detergent, antimicrobial wash, and hard surface cleaner.

The present invention also provides a method of depositing a hydrophobic benefit agent onto a substrate, such as hair, skin, or fabric, comprising contacting the substrate with the consumer product composition of the present invention. Such consumer products can deliver benefits such as hair conditioning, skin moisturizing, fabric softening, or a fabric anti-wrinkle property.

III. Organopolysiloxane Deposition Aid

The pendant organopolysiloxanes of the present invention is represented by the formula:

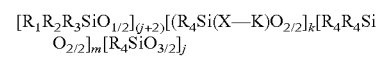

wherein:
  j is an integer from 0 to about 98; in one aspect j is an integer from 0 to about 48; in one aspect, j is 0;
  k is an integer from 1 to about 200, in one aspect k is an integer from 1 to about 50;
  m is an integer from 4 to about 5,000; in one aspect m is an integer from about 10 to about 4,000; in another aspect m is an integer from about 50 to about 2,000;
  $R_1$, $R_2$ and $R_3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy and X—K;
  each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy;

for each X—K X comprises a divalent alkylene radical comprising 2-12 carbon atoms, in one aspect, each divalent alkylene radical is independently selected from the group consisting of —$(CH_2)_s$— wherein s is an integer from 2 to 8, or an integer from 2 to 4; and each K is selected independently from the group consisting of:

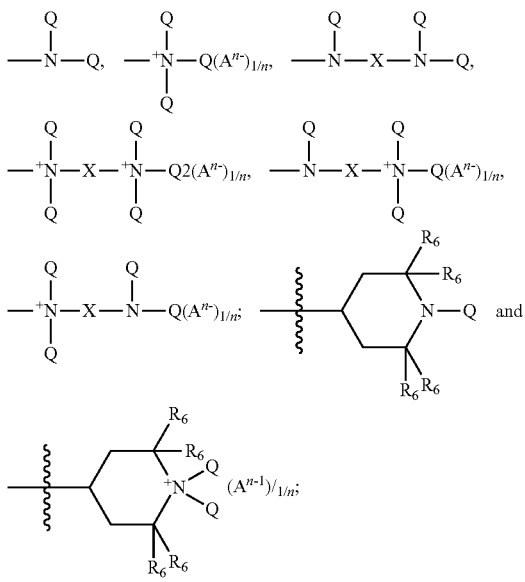

each Q is independently a H or a $C_1$-$C_{32}$, linear or branched, substituted or unsubstituted hydrocarbon, with the proviso that when K is a quat, Q cannot be an amide, imine, or urea moiety and if Q is an amide, imine, or urea moiety, then any additional Q bonded to the same nitrogen as said amide, imine, or urea moiety must be H or a $C_1$-$C_6$ alkyl, in one aspect, said additional Q is H;

X is defined as above;

for K $A^{n-}$ is a suitable charge balancing anion. In one aspect $A^{n-}$ is selected from the group consisting of $Cl^-$, $Br^-$, $I^-$, methylsulfate, toluene sulfonate, carboxylate and phosphate;

for cationically charged K, $A^{n-}$ is a suitable charge balancing anion, in one aspect $A^{n-}$ is selected from the group consisting of $Cl^-$, $Br^-$, $I^-$, methylsulfate, toluene sulfonate, carboxylate and phosphate;

wherein the pendant organopolysiloxane and the benefit agent are identical or different relative to each other.

IV. Methods of Making the Pendant Organopolysiloxane

Embodiments of the present invention can be made as follows. An amount of amino silicone is added to a clean vessel under inert atmosphere. Optionally, a solvent such as isopropanol or tetrahydrofuran is added. The reaction is optionally mixed and quantities of diamine and difunctional organic compounds capable of reacting with the amino functions of the amine compounds are added, either simultaneously or sequentially. For example, the diamine may be added first and the difunctional organic compound capable of reacting with the amino function added second, to obtain the desired organopolysiloxane. Alternately, these reagents may be added in reverse order.

The reaction is run at a temperature appropriate for the reagents. For example, when the difunctional organic compound capable of reacting with the amino functions is a dichloride, the reaction may be run at relatively higher temperatures (typically above 60° C. and often above 80° C.). Alternately, when the difunctional organic compound capable of reacting with the amino functions is a dibromide, the reaction may be run at relatively lower temperatures, including at room temperature (e.g., 21° C.). Alternately, when the difunctional organic compound capable of reacting with the amino functions is an activated dichloride, the reaction may be run at relatively lower temperatures, including at room temperature (e.g., 21° C.). One of ordinary skill in the art would understand the reaction conditions suitable for the specific difunctional organic compound capable of reacting with the amino functions.

The above making process is also generally described by Lange (U.S. Pat. No. 7,563,856). One skilled in the art would understand how the general process disclosed in Lange can be reapplied to the present development in order to produce the pendant organopolysiloxanes of the present invention.

In one embodiment, the reaction is run without the addition of solvent, resulting in a substantially solvent-free process for making the pendant organopolysiloxane of the present invention.

In another embodiment, the reaction is run and subsequently excess amine is added. Without being bound by theory, it is believed that the excess amine will consume the reactive groups of any residual difunctional organic compounds capable of reacting with the amino functions.

In another embodiment, the reaction mixture is further reacted with an amine containing molecule. Non-limiting examples of such amines include ammonia, methylamine, dimethylamine, trimethylamine or triethylamine. Without being bound by theory it is believed that this further reaction caps un-reacted alkyl-halide functionality.

In another embodiment, the reaction mixture is further reacted with a mono-functional organic species capable of reacting with the amine functionality of the pendant organopolysiloxane. Non-limiting examples of such mono-functional organic species include: methyl bromide, methyl iodide, and ethylbromide. Without being bound by theory it is believed that this further reaction helps to quaternize any residual neutral amine groups of the pendant organopolysiloxane, including the terminal amine functionality.

V. Benefit Agents

Benefit agents can be selected from the group consisting of hydrophobic compounds, oils, oil-soluble or dispersible compounds, and water-immiscible compounds, such as those offering hair-care, skin-care, fabric-care, and/or aesthetic or sensory property-boosting benefits.

In the compositions and methods described herein, benefit agents include water-insoluble but oil-soluble/miscible/dispersible solids and liquids, as well as oily materials, that can provide a positive or beneficial effect to the substrate being treated (e.g., to the hair, skin, or fabric). Typical benefit agents can include, but are not limited to, the following: silicone oils, resins, and modifications thereof such as linear and cyclic polydimethylsiloxanes, amino-modified, alkyl, aryl, and alkylaryl silicone oils; fragrance, perfumery, and essential oils and resins; organic sunscreen actives, for example, octylmethoxy cinnamate; antimicrobial agents, for example, 2-hydroxy-4,2,4-trichlorodiphenylether; ester solvents; for example, isopropyl myristate; lipids and lipid like substances, for example, cholesterol; hydrocarbons such as paraffins, petrolatum, and mineral oil; fish and vegetable oils; hydrophobic plant extracts; therapeutic and skin-care agents; waxes; and pigments including inorganic compounds with a hydrophobically modified surface and/or dispersed in an oil or a hydrophobic liquid; and combinations thereof.

In one embodiment, the hydrophobic benefit agent is included in the compositions described herein in an amount from 0.1% to 25%, or from 0.1% to 20%, or from 0.1% to 15, or from 0.1% to 10%, or from 0.1% to 5%, or from 0.1% to 1% or from 0.25% to 25%, or from 0.5% to 20%, or from 1% to 15%, of said emulsion by weight of the consumer product composition.

Silicone Conditioning Agents

Additional conditioning agents, and in particular silicones including non-cationic silicones, may be included in the composition. Conditioning agents include any material which is used to give a particular conditioning benefit to hair and/or skin. In hair treatment compositions, suitable conditioning agents are those which deliver one or more benefits relating to shine, softness, compatibility, antistatic properties, wet-handling, damage, manageability, body, and greasiness. The conditioning agents useful in the compositions of the present invention typically comprise a water insoluble, water dispersible, non-volatile, liquid that forms emulsified, liquid particles. Suitable conditioning agents for use in the composition are those conditioning agents characterized generally as silicones (e.g., silicone oils, cationic silicones, silicone gums, high refractive silicones, and silicone resins), organic conditioning oils (e.g., hydrocarbon oils, polyolefins, and fatty esters) or combinations thereof, or those conditioning agents which otherwise form liquid, dispersed particles in the aqueous surfactant matrix herein. Such conditioning agents should be physically and chemically compatible with the essential components of the composition, and should not otherwise unduly impair product stability, aesthetics or performance.

The concentration of the additional conditioning agent in the composition should be sufficient to provide the desired conditioning benefits, and as will be apparent to one of ordinary skill in the art. Such concentration can vary with the conditioning agent, the conditioning performance desired, the average size of the conditioning agent particles, the type and concentration of other components, and other like factors.

The additional conditioning agent of the compositions of the present invention can be an insoluble silicone conditioning agent. The silicone conditioning agent particles may comprise volatile silicone, non-volatile silicones, or combinations thereof. In one aspect, non-volatile silicones conditioning agents are employed. If volatile silicones are present, it will typically be incidental to their use as a solvent or carrier for commercially available forms of non-volatile silicone materials ingredients, such as silicone gums and resins. The silicone conditioning agent particles may comprise a silicone fluid conditioning agent and may also comprise other ingredients, such as a silicone resin to improve silicone fluid deposition efficiency or enhance glossiness of the hair.

The concentration of the silicone conditioning agent typically ranges from 0.01% to 10%, from 0.1% to 8%, from 0.1% to 5%, or even from 0.2% to 3%. Non-limiting examples of suitable silicone conditioning agents, and optional suspending agents for the silicone, are described in U.S. Reissue Pat. No. 34,584, U.S. Pat. No. 5,104,646, and U.S. Pat. No. 5,106,609. The silicone conditioning agents for use in the compositions of the present invention typically have a viscosity, as measured at 25° C., from 20 centistokes to 2,000,000 centistokes ("cst"), from 1,000 cst to 1,800,000 cst, from 50,000 cst to 1,500,000 cst, or even from 100,000 cst to 1,500,000 csk.

The dispersed silicone conditioning agent particles typically have a number average particle diameter ranging from 0.01 μm to 50 μm. For small particle application to hair, the number average particle diameters typically range from 0.01 μm to 4 μm, from 0.01 μm to 2 μm, or even from 0.01 μm to 0.5 μm. For larger particle application to hair, the number average particle diameters typically range from 4 μm to 50 μm, from 6 μm to 30 μm, from 9 μm to 20 μm, or even from 12 μm to 18 μm.

Silicone fluids may include silicone oils, which are flowable silicone materials having a viscosity, as measured at 25° C., less than 1,000,000 cst, from 5 cst to 1,000,000 cst, or even from 100 cst to 600,000 cst. Suitable silicone oils for use in the compositions of the present invention include polyalkyl siloxanes, polyaryl siloxanes, polyalkylaryl siloxanes, polyether siloxane copolymers, and mixtures thereof. Other insoluble, non-volatile silicone fluids having hair conditioning properties may also be used.

The additional silicone conditioning agent may include an aminosilicone. Aminosilicones, as provided herein, are silicones containing at least one primary amine, secondary amine, tertiary amine, or a quaternary ammonium group. Useful aminosilicones may have less than 0.5% nitrogen by weight of the aminosilicone, less than 0.2%, or even less than 0.1%. Higher levels of nitrogen (amine functional groups) in the amino silicone tend to result in less friction reduction, and consequently less conditioning benefit from the aminosilicone. It should be understood that in some product forms, higher levels of nitrogen are acceptable in accordance with the present invention.

In one aspect, the aminosilicones used in the present invention have a particle size of less than 50μ once incorporated into the final composition. The particle size measurement is taken from dispersed droplets in the final composition. Particle size may be measured by means of a laser light scattering technique, using a Horiba model LA-930 Laser Scattering Particle Size Distribution Analyzer (Horiba Instruments, Inc.).

In one embodiment, the aminosilicone typically has a viscosity of from 1,000 cst (centistokes) to 1,000,000 cst, from 10,000 to 700,000 cst, from 50,000 cst to 500,000 cst, or even from 100,000 cst to 400,000 cst. This embodiment may also comprise a low viscosity fluid, such as, for example, those materials described below in Section F.(1). The viscosity of aminosilicones discussed herein is measured at 25° C.

In another embodiment, the aminosilicone typically has a viscosity of from 1,000 cst to 100,000 cst, from 2,000 cst to 50,000 cst, from 4,000 cst to 40,000 cst, or even from 6,000 cst to 30,000 cs.

The aminosilicone typically is contained in the composition of the present invention at a level by weight of from 0.05% to 20%, from 0.1% to 10%, and or even from 0.3% to 5%.

Other silicone fluids suitable for use in the compositions of the present invention are the insoluble silicone gums and/or resins. Silicone gums are polyorganosiloxane materials having a viscosity, as measured at 25° C., of greater than or equal to 1,000,000 csk. Specific non-limiting examples of silicone gums for use in the compositions of the present invention include polydimethylsiloxane, (polydimethylsiloxane) (methylvinylsiloxane) copolymer, poly(dimethylsiloxane) (diphenyl siloxane)(methylvinylsiloxane) copolymer and mixtures thereof. Silicone resins are highly cross-linked polymeric siloxane systems. The cross-linking is introduced through the incorporation of trifunctional and tetrafunctional silanes with monofunctional or difunctional, or both, silanes during manufacture of the silicone resin.

Silicone materials and silicone resins in particular, can conveniently be identified according to a shorthand nomenclature system known to those of ordinary skill in the art as "MDTQ" nomenclature. Under this system, the silicone is described according to presence of various siloxane monomer units which make up the silicone. Briefly, the symbol M denotes the monofunctional unit $(CH_3)_3SiO_{0.5}$; D denotes the difunctional unit $(CH_3)_2SiO$; T denotes the trifunctional unit $(CH_3)SiO_{1.5}$; and Q denotes the quadra- or tetrafunctional unit $SiO_2$. Primes of the unit symbols (e.g. M', D', T', and Q') denote substituents other than methyl, and must be specifically defined for each occurrence.

In one aspect, silicone resins for use in the compositions of the present invention include, but are not limited to MQ, MT, MTQ, MDT and MDTQ resins. In one aspect, Methyl is a highly suitable silicone substituent. In another aspect, silicone resins are typically MQ resins, wherein the M:Q ratio is typically from 0.5:1.0 to 1.5:1.0 and the average molecular weight of the silicone resin is typically from 1000 to 10,000.

Other non-volatile, insoluble silicone fluid conditioning agents that are suitable for use in the compositions of the present invention are those known as "high refractive index silicones," having a refractive index of at least 1.46, at least 1.48, m at least 1.52, or even at least 1.55. The refractive index of the polysiloxane fluid will generally be less than 1.70, typically less than 1.60. In this context, polysiloxane "fluid" includes oils as well as gums and cyclic silicones. Silicone fluids suitable for use in the compositions of the present invention are disclosed in U.S. Pat. No. 2,826,551, U.S. Pat. No. 3,964,500, and U.S. Pat. No. 4,364,837.

Other modified silicones or silicone copolymers are also useful herein. Examples of these include silicone-based quaternary ammonium compounds (Kennan quats) disclosed in U.S. Pat. Nos. 6,607,717 and 6,482,969; end-terminal quaternary siloxanes; silicone aminopolyalkylene-oxide block copolymers disclosed in U.S. Pat. Nos. 5,807, 956 and 5,981,681; hydrophilic silicone emulsions disclosed in U.S. Pat. No. 6,207,782; and polymers made up of one or more crosslinked rake or comb silicone copolymer segments disclosed in U.S. Pat. No. 7,465,439. Additional modified silicones or silicone copolymers useful herein are described in US Patent Application Nos. 2007/0286837A1 and 2005/0048549A1.

In alternative embodiments of the present invention, the above-noted silicone-based quaternary ammonium compounds may be combined with the silicone polymers described in U.S. Pat. Nos. 7,041,767 and 7,217,777 and US Application number 2007/0041929A1.

Organic Oils

The compositions of the present invention may also comprise from 0.05% to 3%, from 0.08% to 1.5%, or even from 0.1% to 1%, of at least one organic conditioning oil as the conditioning agent, either alone or in combination with other conditioning agents, such as the silicones (described herein). Suitable conditioning oils include hydrocarbon oils, polyolefins, and fatty esters. Suitable hydrocarbon oils include, but are not limited to, hydrocarbon oils having at least 10 carbon atoms, such as cyclic hydrocarbons, straight chain aliphatic hydrocarbons (saturated or unsaturated), and branched chain aliphatic hydrocarbons (saturated or unsaturated), including polymers and mixtures thereof. Straight chain hydrocarbon oils are typically from $C_{12}$ to $C_{19}$. Branched chain hydrocarbon oils, including hydrocarbon polymers, typically will contain more than 19 carbon atoms. Suitable polyolefins include liquid polyolefins, liquid poly-α-olefins, or even hydrogenated liquid poly-α-olefins. Polyolefins for use herein may be prepared by polymerization of $C_4$ to $C_{14}$ or even $C_6$ to $C_{12}$. Suitable fatty esters include, but are not limited to, fatty esters having at least 10 carbon atoms. These fatty esters include esters with hydrocarbyl chains derived from fatty acids or alcohols (e.g. mono-esters, polyhydric alcohol esters, and di- and tri-carboxylic acid esters). The hydrocarbyl radicals of the fatty esters hereof may include or have covalently bonded thereto other compatible functionalities, such as amides and alkoxy moieties (e.g., ethoxy or ether linkages, etc.).

Other Conditioning Agents

Also suitable for use in the compositions herein are the conditioning agents described by the Procter & Gamble Company in U.S. Pat. Nos. 5,674,478, and 5,750,122. Also suitable for use herein are those conditioning agents described in U.S. Pat. Nos. 4,529,586, 4,507,280, 4,663,158, 4,197,865, 4,217, 914, 4,381,919, and 4,422, 853.

Fatty Alcohols, Acids and/or Esters

The compositions of the present invention can comprise a one or more fatty alcohols, acids and esters. The compositions of the present invention can comprise fatty alcohols, acids and/or esters in an amount from 0.05% to 14%, preferably from 0.5% to 10%, and more preferably from 1% to 8%, by weight of the composition.

Fatty alcohols, acids and/or esters suitable for use in the present invention include those having from 18 to 70 carbon atoms, and in one embodiment from 18 to 60 carbon atoms, in another embodiment from 18 to 50 carbon atoms, in yet another embodiment from 18 to 40 carbon atoms, and in even yet another embodiment from 18 to 22 carbon atoms. These fatty alcohols, acids and/or esters may be straight or branched chain alcohols and may be saturated or unsaturated.

Non-limiting examples of suitable fatty alcohols include stearyl alcohol, arachidyl alcohol, behenyl alcohol, C21 fatty alcohol (1-heneicosanol), C23 fatty alcohol (1-tricosanol), C24 fatty alcohol (lignoceryl alcohol, 1-tetracosanol), C26 fatty alcohol (1-hexacosanol), C28 fatty alcohol (1-octacosanol), C30 fatty alcohol (1-triacontanol), C20-40 alcohols (e.g., Performacol 350 and 425 Alcohols, available from New Phase Technologies), C30-50 alcohols (e.g., Performacol 550 Alcohol), C40-60 alcohols (e.g., Performacol 700 Alcohol), and mixtures thereof.

Mixtures of different fatty alcohols comprising one or more fatty alcohols having from 18 to 70 carbon atoms may also comprise some amount of one or more fatty alcohols or other fatty amphiphiles which have less than 18 carbon atoms or greater than 70 carbon atoms and still be considered to be within the scope of the present invention, provided that the resulting dispersed gel network phase has a melt transition temperature of at least 38 deg. C. Such fatty alcohols suitable for use in the present invention may be of natural or vegetable origin, or they may be of synthetic origin.

Anti-Dandruff Actives

The compositions of the present invention may also contain an anti-dandruff agent. Suitable, non-limiting examples of anti-dandruff actives include: antimicrobial actives, pyridinethione salts, azoles, selenium sulfide, particulate sulfur, keratolytic acid, salicylic acid, octopirox (piroctone olamine), coal tar, and combinations thereof. In one aspect, the anti-dandruff actives typically are pyridinethione salts. Such anti-dandruff particulate should be physically and chemically compatible with the essential components of the composition, and should not otherwise unduly impair product stability, aesthetics or performance.

Pyridinethione anti-dandruff agents are described, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982. It is contemplated that when ZPT is used as the anti-dandruff particulate in the compositions herein, that the growth or re-growth of hair may be stimulated or regulated, or both, or that hair loss may be reduced or inhibited, or that hair may appear thicker or fuller.

Humectants

The compositions of the present invention may contain a humectant. The humectants herein are selected from the group consisting of polyhydric alcohols, water soluble alkoxylated nonionic polymers, and mixtures thereof. The humectants, when used herein, are typically used at levels of from 0.1% to 20%, or even from 0.5% to 5%.

Skin Care Actives

The composition may comprise at least one skin care active, useful for regulating and/or improving the condition and/or appearance of mammalian skin. The skin care active may be soluble in oil or water, and may be present primarily in the oil phase and/or in the aqueous phase. Suitable actives include, but are not limited to, vitamins, peptides, sugar amines, sunscreens, oil control agents, tanning actives, anti-acne actives, desquamation actives, anti-cellulite actives, chelating agents, skin lightening agents, flavonoids, protease inhibitors, non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, and antifungals.

The composition may comprise from 0.001% to 10%, alternatively from 0.01% to 5%, of at least one vitamin. Herein, "vitamins" means vitamins, pro-vitamins, and their salts, isomers and derivatives. Non-limiting examples of suitable vitamins include: vitamin B compounds (including B1 compounds, B2 compounds, B3 compounds such as niacinamide, niacinnicotinic acid, tocopheryl nicotinate, $C_1$-$C_{18}$ nicotinic acid esters, and nicotinyl alcohol; B5 compounds, such as panthenol or "pro-B5", pantothenic acid, pantothenyl; B6 compounds, such as pyroxidine, pyridoxal, pyridoxamine; carnitine, thiamine, riboflavin); vitamin A compounds, and all natural and/or synthetic analogs of Vitamin A, including retinoids, retinol, retinyl acetate, retinyl palmitate, retinoic acid, retinaldehyde, retinyl propionate, carotenoids (pro-vitamin A), and other compounds which possess the biological activity of Vitamin A; vitamin D compounds; vitamin K compounds; vitamin E compounds, or tocopherol, including tocopherol sorbate, tocopherol acetate, other esters of tocopherol and tocopheryl compounds; vitamin C compounds, including ascorbate, ascorbyl esters of fatty acids, and ascorbic acid derivatives, for example, ascorbyl phosphates such as magnesium ascorbyl phosphate and sodium ascorbyl phosphate, ascorbyl glucoside, and ascorbyl sorbate; and vitamin F compounds, such as saturated and/or unsaturated fatty acids. In one embodiment, the composition may comprise a vitamin selected from the group consisting of vitamin B compounds, vitamin C compounds, vitamin E compounds and mixtures thereof. Alternatively, the vitamin is selected from the group consisting of niacinamide, tocopheryl nicotinate, pyroxidine, panthenol, vitamin E, vitamin E acetate, ascorbyl phosphates, ascorbyl glucoside, and mixtures thereof.

The composition may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide refers to both naturally occurring and synthesized peptides. In one embodiment, the peptides are di-, tri-, tetra-, penta-, and hexa-peptides, their salts, isomers, derivatives, and mixtures thereof. Examples of useful peptide derivatives include, but are not limited to, peptides derived from soy proteins, carnosine (beta-alanine-histidine), palmitoyl-lysine-threonine (pal-KT) and palmitoyl-lysine-threonine-threonine-lysine-serine (pal-KTTKS, available in a composition known as MATRIXYL®), palmitoyl-glycine-glutamine-proline-arginine (pal-GQPR, available in a composition known as RIGIN®), these three being available from Sederma, France, acetyl-glutamate-glutamate-methionine-glutamine-arginine-arginine (Ac-EEMQRR; Argireline®), and Cu-histidine-glycine-glycine (Cu-HGG, also known as IAMIN®). The compositions may comprise from $1 \times 10^{-7}$% to 20%, alternatively from $1 \times 10^{-6}$% to 10%, and alternatively from $1 \times 10^{-5}$% to 5% of the peptide.

The composition may comprise a sugar amine, also known as amino sugars, and their salts, isomers, tautomers and derivatives. Sugar amines can be synthetic or natural in origin and can be used as pure compounds or as mixtures of compounds (e.g., extracts from natural sources or mixtures of synthetic materials). For example, glucosamine is generally found in many shellfish and can also be derived from fungal sources. Examples of sugar amines include glucosamine, N-acetyl glucosamine, mannosamine, N-acetyl mannosamine, galactosamine, N-acetyl galactosamine, their isomers (e.g., stereoisomers), and their salts (e.g., HCl salt). Other sugar amine compounds useful in skin care compositions include those described in U.S. Pat. No. 6,159,485, issued to Yu, et al. In one embodiment, the composition may comprise from 0.01% to 15%, alternatively from 0.1% to 10%, and alternatively from 0.5% to 5%, of the sugar amine.

The composition may comprise one or more sunscreen actives (or sunscreen agents) and/or ultraviolet light absorbers. Herein, suitable sunscreen actives include oil-soluble sunscreens, insoluble sunscreens, and water-soluble sunscreens. In certain embodiments, the composition may comprise from 1% to 20%, or, alternatively, from 2% to 10%, by weight of the composition, of the sunscreen active and/or ultraviolet light absorber. Exact amounts will vary depending upon the chosen sunscreen active and/or ultraviolet light absorber and the desired Sun Protection Factor (SPF), and are within the knowledge and judgment of one of skill in the art.

Non-limiting examples of suitable oil-soluble sunscreens include benzophenone-3, bis-ethylhexyloxyphenol methoxyphenyl triazine, butyl methoxydibenzoyl-methane, diethylamino hydroxy-benzoyl hexyl benzoate, drometrizole trisiloxane, ethylhexyl methoxy-cinnamate, ethylhexyl salicylate, ethylhexyl triazone, octocrylene, homosalate, polysilicone-15, and derivatives and mixtures thereof.

Non-limiting examples of suitable insoluble sunscreens include methylene bis-benzotriazolyl tetramethylbutyl-phenol, titanium dioxide, zinc cerium oxide, zinc oxide, and derivatives and mixtures thereof.

Non-limiting examples of suitable water-soluble sunscreens include phenylbenzimidazole sulfonic acid (PBSA), terephthalylidene dicamphor sulfonic acid, (Mexoryl™ SX), benzophenone-4, benzophenone-5, benzylidene camphor sulfonic acid, cinnamidopropyl-trimonium chloride, methoxycinnamido-propyl ethyldimonium chloride ether, disodium bisethylphenyl triaminotriazine stilbenedisulfonate, disodium distyrylbiphenyl disulfonate, disodium phenyl dibenzimidazole tetrasulfonate, methoxycinnamido-propyl hydroxysultaine, methoxycinnamido-propyl laurdimonium tosylate, PEG-25 PABA (p-aminobenzoic acid), polyquaternium-59, TEA-salicylate, and salts, derivatives and mixtures thereof.

The composition may comprise one or more compounds for regulating the production of skin oil, or sebum, and for improving the appearance of oily skin. Examples of suitable oil control agents include salicylic acid, dehydroacetic acid, benzoyl peroxide, vitamin B3 compounds (for example, niacinamide or tocopheryl nicotinate), their isomers, esters, salts and derivatives, and mixtures thereof. The compositions may comprise from 0.0001% to 15%, alternatively from 0.01% to 10%, alternatively from 0.1% to 5%, and alternatively from 0.2% to 2%, of an oil control agent.

The composition may comprise a tanning active. The compositions may comprise from 0.1% to 20%, from 2% to 7%, or, alternatively, from 3% to 6%, by weight of the composition, of a tanning active. A suitable tanning active includes dihydroxyacetone, which is also known as DHA or 1,3-dihydroxy-2-propanone.

The composition may comprise a safe and effective amount of one or more anti-acne actives. Examples of useful anti-acne actives include resorcinol, sulfur, salicylic acid, erythromycin, zinc, and benzoyl peroxide. Suitable anti-acne actives are described in further detail in U.S. Pat. No. 5,607,980. The composition may comprise a safe and effective amount of a desquamation active such as from 0.01% to 10%, from 0.5% to 5%, or, alternatively, from 0.1% to 2%, by weight of the composition. For example, the desquamation actives tend to improve the texture of the skin (e.g., smoothness). A suitable desquamation system may comprise sulfhydryl compounds and zwitterionic surfactants and is described in U.S. Pat. No. 5,681,852. Another suitable desquamation system may comprise salicylic acid and zwitterionic surfactants and is described in U.S. Pat. No. 5,652,228.

The composition may comprise a safe and effective amount of an anti-cellulite agent. Suitable agents may include, but are not limited to, xanthine compounds (e.g., caffeine, theophylline, theobromine, and aminophylline).

Skin care compositions may comprise a safe and effective amount of a chelating agent such as from 0.1% to 10% or from 1% to 5% of the composition. Exemplary chelators are disclosed in U.S. Pat. No. 5,487,884. A suitable chelator is furildioxime and derivatives.

The composition may comprise a skin lightening agent. The compositions may comprise from 0.1% to 10%, from 0.2% to 5%, or, alternatively, from 0.5% to 2%, by weight of the composition, of a skin lightening agent. Suitable skin lightening agents include kojic acid, arbutin, tranexamic acid, ascorbic acid and derivatives (e.g., magnesium ascorbyl phosphate or sodium ascorbyl phosphate or other salts of ascorbyl phosphate), ascorbyl glucoside, and the like. Other suitable skin lightening materials include undecylenoyl phenylalanine (Sepiwhite® from SEPPIC), aloesin, Actiwhite® (Cognis), and Emblica® (Rona).

The composition compositions may comprise a flavonoid. The flavonoid can be synthetic materials or obtained as extracts from natural sources, which also further may be derivatized. Examples of classes of suitable flavonoids are disclosed in U.S. Pat. No. 6,235,773.

The composition may comprise protease inhibitors including, but are not limited to, hexamidine compounds, vanillin acetate, menthyl anthranilate, soybean trypsin inhibitor, Bowman-Birk inhibitor, and mixtures thereof. Skin care compositions can include hexamidine compounds, its salts, and derivatives. As used herein, "hexaminide compound" means a compound having the formula:

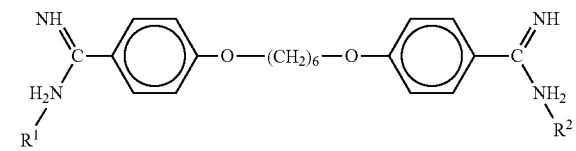

wherein $R^1$ and $R^2$ are optional or are organic acids (e.g., sulfonic acids, etc.). A particularly suitable hexamidine compound is hexamidine diisethionate.

The composition may other optional components such as non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobial or antifungal actives, and other useful skin care actives, which are described in further detail in U.S. application publication No. US 2006/0275237A1 and US 2004/0175347A1.

Fabric Softening Active Compounds

The fabric or home care compositions of the current invention may comprise a fabric softening active. Said fabric softening active may comprise, as the principal active, compounds of the following formula:

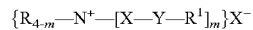

wherein each R may comprise either hydrogen, a short chain $C_1$-$C_6$, in one aspect a $C_1$-$C_3$ alkyl or hydroxyalkyl group, for example methyl, ethyl, propyl, hydroxyethyl, and the like, poly($C_{2-3}$ alkoxy), polyethoxy, benzyl, or mixtures thereof; each X may independently be $(CH_2)_n$, $CH_2$—CH($CH_3$)— or CH—($CH_3$)—$CH_2$—; each Y may comprise —O—(O)C—, —C(O)—O—, —NR—C(O)—, or —C(O)—NR—; each m may be 2 or 3; each n may be from 1 to 4, in one aspect 2; the sum of carbons in each $R^1$, plus one when Y is —O—(O)C— or —NR—C(O)—, may be $C_{12}$-$C_{22}$, or $C_{14}$-$C_{20}$, with each $R^1$ being a hydrocarbyl, or substituted hydrocarbyl group; and $X^-$ may comprise any softener-compatible anion. In one aspect, the softener-compatible anion may comprise chloride, bromide, methylsulfate, ethylsulfate, sulfate, and nitrate. In another aspect, the softener-compatible anion may comprise chloride or methyl sulfate.

In another aspect, the fabric softening active may comprise the general formula:

wherein each Y, R, $R^1$, and $X^-$ have the same meanings as those specified for the fabric softening active immediately above. Such compounds include those having the formula:

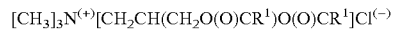

wherein each R may comprise a methyl or ethyl group. In one aspect, each $R^1$ may comprise a $C_{15}$ to $C_{19}$ group. As used herein, when the diester is specified, it can include the monoester that is present.

These types of agents and general methods of making them are disclosed in U.S. Pat. No. 4,137,180. An example of a suitable "propyl" ester quaternary ammonium fabric softener active comprising the formula 1,2-di(acyloxy)-3-trimethylammoniopropane chloride.

In one aspect, the fabric softening active may comprise the formula:

$[R_{4-m}—N^+—R^1_m]X^-$ wherein each R, $R^1$, m and $X^-$ have the same meanings specified in relation to the fabric softening active prior.

In a further aspect, the fabric softening active may comprise the formula:

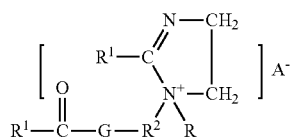

wherein each R and $R^1$ have the definitions given to the fabric softening active above; $R^2$ may comprise a $C_{1-6}$ alkylene group, in one aspect an ethylene group; and G may comprise an oxygen atom or an —NR— group; and $A^-$ is as defined below.

In a yet further aspect, the fabric softening active may comprise the formula:

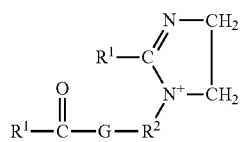

wherein $R^1$, $R^2$ and G are defined as above.

In a further aspect, the fabric softening active may comprise condensation reaction products of fatty acids with dialkylenetriamines in, e.g., a molecular ratio of 2:1.

Non-limiting examples of such fabric softening actives include are N,N-bis(stearoyl-oxy-ethyl) N,N-dimethyl ammonium chloride, N,N-bis(tallowoyl-oxy-ethyl) N,N-dimethyl ammonium chloride, N,N-bis(stearoyl-oxy-ethyl) N-(2 hydroxyethyl) N-methyl ammonium methylsulfate.

It will be understood that combinations of softener actives disclosed above are suitable for use herein.

It can be understood by one of skill in the art that the cationic optional fabric softener actives herein further comprise counter ions such as anions, that provide electrical neutrality. Most often, the anion used to provide electrical neutrality in these salts is from a strong acid, especially a halide, such as chloride, bromide, or iodide. However, other anions can be used, such as methylsulfate, ethylsulfate, acetate, formate, sulfate, carbonate, and the like. In one aspect, the anion may comprise chloride or methylsulfate. The anion, in some aspects, may carry a double or multiple charge.

In one aspect, the fabric care and/or treatment composition may comprise a second softening agent selected from the group consisting of polyglycerol esters (PGEs), oily sugar derivatives, and wax emulsions. Suitable PGEs include those disclosed in U.S. PA 61/089,080. Suitable oily sugar derivatives and wax emulsions include those disclosed in USPA 2008-0234165 A1.

In one aspect, the compositions may comprise from 0.001% to 0.01% of an unsaturated aldehyde. In one aspect, the compositions are essentially free of an unsaturated aldehyde. Without being limited by theory, in this aspect, the compositions are less prone to the yellowing effect often encountered with amino-containing agents.

Perfume

The optional perfume component may comprise a component selected from the group consisting of perfume oils, mixtures of perfume oils, perfume microcapsules, pressure-activated perfume microcapsules, moisture-activated perfume microcapsules and mixtures thereof. Said perfume microcapsule compositions may comprise from 0.05% to 5%; or from 0.1% to 1% of an encapsulating material. In turn, the perfume core may comprise a perfume and optionally a diluent.

Pressure-activated perfume microcapsules generally comprise core-shell configurations in which the core material further comprises a perfume oil or mixture of perfume oils. The shell material surrounding the core to form the microcapsule can be any suitable polymeric material which is impervious or substantially impervious to the materials in the core (generally a liquid core) and the materials which may come in contact with the outer substrate of the shell. In one aspect, the material making the shell of the microcapsule may comprise formaldehyde. Formaldehyde based resins such as melamine-formaldehyde or urea-formaldehyde resins are especially attractive for perfume encapsulation due to their wide availability and reasonable cost.

Moisture-activated perfume microcapsules, comprising a perfume carrier and an encapsulated perfume composition, wherein said perfume carrier may be selected from the group consisting of cyclodextrins, starch microcapsules, porous carrier microcapsules, and mixtures thereof; and wherein said encapsulated perfume composition may comprise low volatile perfume ingredients, high volatile perfume ingredients, and mixtures thereof;

(1) a pro-perfume;
(2) a low odor detection threshold perfume ingredients, wherein said low odor detection threshold perfume ingredients may comprise less than 25%, by weight of the total neat perfume composition; and
(3) mixtures thereof.

A suitable moisture-activated perfume carrier that may be useful in the disclosed multiple use fabric conditioning composition may comprise cyclodextrin. As used herein, the term "cyclodextrin" includes any of the known cyclodextrins such as unsubstituted cyclodextrins containing from six to twelve glucose units, especially beta-cyclodextrin, gamma-cyclodextrin, alpha-cyclodextrin, and/or derivatives thereof, and/or mixtures thereof. A more detailed description of suitable cyclodextrins is provided in U.S. Pat. No. 5,714,137. Suitable cylodextrins herein include beta-cyclodextrin, gamma-cyclodextrin, alpha-cyclodextrin, substituted beta-cyclodextrins, and mixtures thereof. In one aspect, the cyclodextrin may comprise beta-cyclodextrin. Perfume molecules are encapsulated into the cavity of the cyclodextrin molecules to form molecular microcapsules, commonly referred to as cyclodextrin/perfume complexes. The perfume loading in a cyclodextrin/perfume complex may comprise from 3% to 20%, or from 5% to 18%, or from 7% to 16%, by weight of the cyclodextrin/perfume complex.

The cyclodextrin/perfume complexes hold the encapsulated perfume molecules tightly, so that they can prevent perfume diffusion and/or perfume loss, and thus reducing the odor intensity of the multiple use fabric conditioning composition. However, the cyclodextrin/perfume complex can readily release some perfume molecules in the presence of moisture, thus providing a long lasting perfume benefit. Non-limiting examples of preparation methods are given in U.S. Pat. Nos. 5,552,378, and 5,348,667.

Dye Transfer Inhibiting Agents

The compositions may also include from 0.0001%, from 0.01%, from 0.05% by weight of the compositions to 10%, 2%, or even 1% by weight of the compositions of one or more dye transfer inhibiting agents such as polyvinylpyrrolidone polymers, polyamine N-oxide polymers, copolymers of N-vinylpyrrolidone and N-vinylimidazole, polyvinyloxazolidones and polyvinylimidazoles or mixtures thereof.

Brighteners

The compositions may also comprise a brightener (also referred to as "optical brightener") and may include any compound that exhibits fluorescence, including compounds that absorb UV light and reemit as "blue" visible light. Non-limiting examples of useful brighteners include: derivatives of stilbene or 4,4'-diaminostilbene, biphenyl, five-membered heterocycles such as triazoles, pyrazolines, oxazoles, imidiazoles, etc., or six-membered heterocycles (coumarins, naphthalamide, s-triazine, etc.). Cationic, anionic, nonionic, amphoteric and zwitterionic brighteners can be used. Suitable brighteners include those commercially marketed under the trade name Tinopal-UNPA-GX® by Ciba Specialty Chemicals Corporation (High Point, N.C.).

Bleach System

Bleach systems suitable for use herein contain one or more bleaching agents. Non-limiting examples of suitable bleaching agents include catalytic metal complexes; activated peroxygen sources; bleach activators; bleach boosters; photobleaches; bleaching enzymes; free radical initiators; $H_2O_2$; hypohalite bleaches; peroxygen sources, including perborate and/or percarbonate and combinations thereof. Suitable bleach activators include perhydrolyzable esters and perhydrolyzable imides such as, tetraacetyl ethylene diamine, octanoylcaprolactam, benzoyloxybenzenesulphonate, nonanoyloxybenzene¬ sulphonate, benzoylvalerolactam, dodecanoyloxybenzenesulphonate. Suitable bleach boosters include those described in U.S. Pat. No. 5,817,614. Other bleaching agents include metal complexes of transitional metals with ligands of defined stability constants. Such catalysts are disclosed in U.S. Pat. Nos. 4,430,243, 5,576,282, 5,597,936 and 5,595,967.

VI. Optional Adjuncts

The compositions may additionally comprise one or more adjunct materials, as desired for the particular product form. For the purposes of the present invention, the non-limiting list of adjuncts illustrated hereinafter are suitable for use in the instant compositions and may be desirably incorporated in certain embodiments of the invention, for example to assist or enhance performance, for treatment of the substrate to be cleaned, or to modify the aesthetics of the composition as is the case with perfumes, colorants, dyes or the like. It is understood that such adjuncts are in addition to the components that are supplied via Applicants' perfumes and/or perfume systems. The precise nature of these additional components, and levels of incorporation thereof, will depend on the physical form of the composition and the nature of the operation for which it is to be used. Suitable adjunct materials include, but are not limited to, surfactants, builders, chelating agents, dye transfer inhibiting agents, dispersants, enzymes, and enzyme stabilizers, catalytic materials, bleach activators, polymeric dispersing agents, clay soil removal/anti-redeposition agents, brighteners, suds suppressors, dyes, additional perfume and perfume delivery systems, structure elasticizing agents, fabric softeners, carriers, hydrotropes, processing aids and/or pigments. In addition to the disclosure below, suitable examples of such other adjuncts and levels of use are found in U.S. Pat. Nos. 5,576,282, 6,306,812 B1 and 6,326,348 B1 that are incorporated by reference.

It should be noted that the benefit agents discussed above and the adjuncts set forth herein can, in many instances, function as both an optional adjunct and as a benefit agent. Further, a benefit agent could instead serve the function of an optional adjunct, and vice versa, depending upon the desired end use benefits. Therefore, one list is not exclusive of the other, but rather they overlap.

The following list of materials is representative of the various ingredients suitable for use in formulating various consumer product compositions of the present invention, but is in no way meant to be limiting or exhaustive.

Hydrophilic Solvents

Hydrophilic solvents suitable for use include water and hydrophilic organic liquids and mixtures thereof. Nonlimiting examples of hydrophilic organic liquids include glycerol, ethanol, isopropanol, propylene glycol, butylene glycol, hexylene glycol, polyethylene glycol and mixtures thereof. In one embodiment, the hydrophilic solvent is selected from the group consisting of water, alcohols, glycols, glycerine, and combinations thereof.

In one embodiment, the level of hydrophilic solvent may range from 0.1% to 95%, or from 1 to 90%, or from 3 to 90% by weight of the consumer product compositions.

Surfactants

The compositions of the present invention may comprise one or more surfactants. The surfactant component is included in personal care compositions of the present invention to provide cleansing performance. The surfactant may be selected from anionic surfactant, zwitterionic or amphoteric surfactant, or a combination thereof. Suitable surfactant components for use in the composition herein include those which are known for use in hair care, fabric care, surface care or other personal care and/or home care cleansing compositions.

Suitable nonionic surfactants include, but not limited to, aliphatic, primary or secondary linear or branched chain alcohols or phenols with alkylene oxides, generally ethylene oxide and generally 6-30 ethylene oxide groups. Other suitable nonionic surfactants include mono- or di-alkyl alkanolamides, alkyl polyglucosides, and polyhydroxy fatty acid amides.

Non-limiting examples of suitable anionic surfactants are the sodium, ammonium, and mono-, di-, and tri-ethanolamine salts of alkyl sulfates, alkyl ether sulfates, alkaryl sulfonates, alkyl succinates, alkyl sulfosuccinate, N-alkoyl sarcosinates, alkyl phosphates, alkyl ether phosphates, alkyl ether carboxylates, and alpha-olefin sulfonates. The alkyl groups generally contain from 8 to 18 carbon atoms and may be unsaturated. The alkyl ether sulfates, alkyl ether phosphates, and alkyl ether carboxylates may contain from 1 to 10 ethylene oxide or propylene oxide units per molecule, and preferably contain 2 to 3 ethylene oxide units per molecule. Examples of anionic surfactants include sodium or ammonium lauryl sulfate and sodium or ammonium lauryl ether sulfate. Suitable anionic surfactants useful in the current invention are generally used in a range from 5% to 50%, preferably from 8% to 30%, more preferably from 10% to 25%, even more preferably from 12% to 22%, by weight of the composition.

Nonlimiting examples of suitable cationic surfactants include water-soluble or water-dispersible or water-insoluble compounds containing at least one amine group which is preferably a quaternary amine group, and at least one hydrocarbon group which is preferably a long-chain hydrocarbon group. The hydrocarbon group may be hydroxylated and/or alkoxylated and may comprise ester- and/or amido- and/or aromatic-groups. The hydrocarbon group may be fully saturated or unsaturated.

In one embodiment, the level of surfactant may range from 0.5% to 95%, or from 2% to 90%, or from 3% to 90% by weight of the consumer product compositions.

Suitable zwitterionic or amphoteric surfactants for use in the composition herein include those which are known for use in hair care or other personal cleansing compositions. Concentration of such amphoteric surfactants preferably ranges from 0.5% to 20%, preferably from 1% to 10%. Non-limiting examples of suitable zwitterionic or amphoteric surfactants are described in U.S. Pat. Nos. 5,104,646 and 5,106,609, both to Bolich, Jr. et al.

The amphoteric surfactants suitable for use in the present invention can include alkyl amine oxides, alkyl betaines, alkyl amidopropyl betaines, alkyl sulfobetaines, alkyl glycinates, alkyl carboxyglycinates, alkyl amphopropionates, alkyl amidopropyl hydroxysultaines, acyl taurates, and acyl glutamates wherein the alkyl and acyl groups have from 8 to 18 carbon atoms.

Non-liming examples of other anionic, zwitterionic, amphoteric, cationic, nonionic, or optional additional surfactants suitable for use in the compositions are described in McCutcheon's, Emulsifiers and Detergents, 1989 Annual, published by M. C. Publishing Co., and U.S. Pat. Nos. 3,929,678; 2,658,072; 2,438,091; and 2,528,378.

Suspending Agent

The compositions of the present invention may further comprise a suspending agent at concentrations effective for suspending water-insoluble material in dispersed form in the compositions or for modifying the viscosity of the composition. Such concentrations range from 0.1% to 10%, or even from 0.3% to 5.0%.

Pigments

The compositions of the present invention may also contain pigment materials such as inorganic, nitroso, monoazo, disazo, carotenoid, triphenyl methane, triaryl methane, xanthene, quinoline, oxazine, azine, anthraquinone, indigoid, thioindigoid, quinacridone, phthalocianine, botanical, natural colors, including: water soluble components such as those having C. I. Names.

Gel Matrix

In some embodiments, the fatty alcohols, may be present in the form of a dispersed gel network phase (i.e., as a phase which is incorporated and dispersed into the final composition). In one embodiment, a secondary cationic surfactant, together with high melting point fatty compounds and an aqueous carrier, form a gel matrix. The gel matrix is suitable for providing various conditioning benefits such as slippery feel during the application to wet hair and softness and moisturized feel on dry hair.

The compositions of the present invention can comprise a dispersed fatty alcohol gel network phase in an amount greater than 0.1%, preferably from 1% to 60%, and more preferably from 5% to 40%, by weight of the composition.

The gel network component of the present invention can comprise a secondary surfactant. As used herein, "secondary surfactant" refers to one or more surfactants which are combined with the fatty alcohol and water to form the gel network of the present invention as a pre-mix separate from the other components of the shampoo composition. The secondary surfactant is separate from and in addition to any emulsifying surfactant and/or any surfactant of the personal care composition. However, the secondary surfactant may be the same or different type of surfactant or surfactants as that or those selected for the surfactant component described above.

The compositions of the present invention can comprise secondary surfactant as part of the pre-formed dispersed gel network phase in an amount from 0.01% to 15%, preferably from 0.1% to 10%, and more preferably from 0.3% to 5%, by weight of the shampoo composition.

Suitable secondary surfactants include anionic, zwitterionic, amphoteric, cationic, and nonionic surfactants. Preferably, the secondary surfactant is selected from anionic, cationic, and nonionic surfactants, and mixtures thereof. For additional discussion of secondary surfactants which are suitable for use in the present invention, see U.S. 2006/0024256 A1.

Additionally, in an embodiment of the present invention, certain secondary surfactants which have a hydrophobic tail group with a chain length of from 16 to 22 carbon atoms may be selected to contribute to obtaining a melt transition temperature of at least 38 deg. C. for the resulting dispersed gel network phase. For such secondary surfactants, the hydrophobic tail group may be alkyl, alkenyl (containing up to 3 double bonds), alkyl aromatic, or branched alkyl. In such an embodiment, it is preferred that the secondary surfactant is present in the gel network component relative to the fatty alcohol at a weight ratio from 1:5 to 5:1. Mixtures of more than one surfactant of the above specified types may be used for the secondary surfactant of the present invention.

In one embodiment of the gel matrix, the secondary surfactant may be a cationic surfactant and the cationic secondary surfactant and the high melting point fatty compound may be contained at a level such that the weight ratio of the cationic surfactant to the high melting point fatty compound is in the range of from 1:1 to 1:10, or even from 1:1 to 1:6.

The gel network component may also comprise water or suitable solvents. The water or suitable solvent and the secondary surfactant together contribute to the swelling of the fatty alcohol. This, in turn, leads to the formation and the stability of the gel network. As used herein, the term "suitable solvent" refers to any solvent which can be used in the place of or in combination with water in the formation of the gel network of the present invention.

The compositions of the present invention comprise water or suitable solvents as part of the pre-formed dispersed gel network phase in an amount suitable to achieve a gel network when combined with fatty alcohol and secondary surfactant according to the present invention. In one embodiment, the compositions of the present invention comprise as part of the pre-formed dispersed gel network phase at least 0.05% of water or a suitable solvent, by weight of the shampoo composition. In another embodiment, the compositions comprise water or a suitable solvent as part of the pre-formed dispersed gel network phase is an amount relative to the amount of fatty alcohol at a weight ratio of at least 1:1.

Builders

The compositions may also contain from 0.1% to 80% by weight of a builder. Compositions in liquid form generally contain from 1% to 10% by weight of the builder component. Compositions in granular form generally contain from 1% to 50% by weight of the builder component. Detergent builders are well known in the art and can contain, for example, phosphate salts as well as various organic and inorganic nonphosphorus builders. Water-soluble, nonphosphorus organic builders useful herein include the various alkali metal, ammonium and substituted ammonium polyacetates, carboxylates, polycarboxylates and polyhydroxy sulfonates. Examples of polyacetate and polycarboxylate builders are the sodium, potassium, lithium, ammonium and substituted ammonium salts of ethylene diamine tetraacetic acid, nitrilotriacetic acid, oxydisuccinic acid, mellitic acid, benzene polycarboxylic acids, and citric acid. Other suitable polycarboxylates for use herein are the polyacetal carboxylates described in U.S. Pat. No. 4,144,226 and U.S. Pat. No. 4,246,495. Other polycarboxylate builders are the oxydisuccinates and the ether carboxylate builder compositions comprising a combination of tartrate monosuccinate and tartrate disuccinate described in U.S. Pat. No. 4,663,071, Builders for use in liquid detergents are described in U.S. Pat. No. 4,284,532, One suitable builder includes may be citric acid. Suitable nonphosphorus, inorganic builders include the silicates, aluminosilicates, borates and carbonates, such as sodium and potassium carbonate, bicarbonate, sesquicarbonate, tetraborate decahydrate, and silicates having a weight ratio of SiO2 to alkali metal oxide of from 0.5 to 4.0, or from 1.0 to 2.4. Also useful are aluminosilicates including zeolites. Such materials and their use as detergent builders are more fully discussed in U.S. Pat. No. 4,605,509.

Dispersants

The compositions may contain from 0.1%, to 10%, by weight of dispersants Suitable water-soluble organic materials are the homo- or co-polymeric acids or their salts, in which the polycarboxylic acid may contain at least two carboxyl radicals separated from each other by not more than two carbon atoms. The dispersants may also be alkoxylated derivatives of polyamines, and/or quaternized derivatives thereof such as those described in U.S. Pat. Nos. 4,597,898, 4,676,921, 4,891,160, 4,659,802 and 4,661,288.

Enzymes

The compositions may contain one or more detergent enzymes which provide cleaning performance and/or fabric care benefits. Examples of suitable enzymes include hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. A typical combination may be a cocktail of conventional applicable enzymes like protease, lipase, cutinase and/or cellulase in conjunction with amylase. Enzymes can be used at their art-taught levels, for example at levels recommended by suppliers such as Novozymes and Genencor. Typical levels in the compositions are from 0.0001% to 5%. When enzymes are present, they can be used at very low levels, e.g., from 0.001% or lower; or they can be used in heavier-duty laundry detergent formulations at higher levels, e.g., 0.1% and higher. In accordance with a preference of some consumers for "non-biological" detergents, the compositions may be either or both enzyme-containing and enzyme-free.

Chelant

The compositions may contain less than 5%, or from 0.01% to 3% of a chelant such as citrates; nitrogen-containing, P-free aminocarboxylates such as EDDS, EDTA and DTPA; aminophosphonates such as diethylenetriamine pentamethylenephosphonic acid and, ethylenediamine tetramethylenephosphonic acid; nitrogen-free phosphonates e.g., HEDP; and nitrogen or oxygen containing, P-free carboxylate-free chelants such as compounds of the general class of certain macrocyclic N-ligands such as those known for use in bleach catalyst systems.

Stabilizer

The compositions may contain one or more stabilizers and thickeners. Any suitable level of stabilizer may be of use; exemplary levels include from 0.01% to 20%, from 0.1% to 10%, or from 0.1% to 3% by weight of the composition. Non-limiting examples of stabilizers suitable for use herein include crystalline, hydroxyl-containing stabilizing agents, trihydroxystearin, hydrogenated oil, or a variation thereof, and combinations thereof. In some aspects, the crystalline, hydroxyl-containing stabilizing agents may be water-insoluble wax-like substances, including fatty acid, fatty ester or fatty soap. In other aspects, the crystalline, hydroxyl-containing stabilizing agents may be derivatives of castor oil, such as hydrogenated castor oil derivatives, for example, castor wax. The hydroxyl containing stabilizers are disclosed in U.S. Pat. Nos. 6,855,680 and 7,294,611. Other stabilizers include thickening stabilizers such as gums and other similar polysaccharides, for example gellan gum, carrageenan gum, and other known types of thickeners and rheological additives. Exemplary stabilizers in this class include gum-type polymers (e.g. xanthan gum), polyvinyl alcohol and derivatives thereof, cellulose and derivatives thereof including cellulose ethers and cellulose esters and tamarind gum (for example, comprising xyloglucan polymers), guar gum, locust bean gum (in some aspects comprising galactomannan polymers), and other industrial gums and polymers.

Other Ingredients

Depending on the form of consumer product in which they are used (e.g., shampoo, liquid soap, bodywash, laundry detergent, fabric softener), these compositions may further contain ingredients selected from fatty alcohols having 8 to 22 carbon atoms, opacifiers or pearlescers such as ethylene glycol esters of fatty acids (e.g., ethylene glycol distearate), viscosity modifiers, buffering or pH adjusting chemicals, water-soluble polymers including cross-linked and non cross-linked polymers, foam boosters, perfumes, dyes, coloring agents or pigments, herb extracts, preservatives, hydrotopes, enzymes, bleaches, fabric conditioners, optical brighteners, antioxidants, stabilizers, dispersants, soil release agents, anti-wrinkle agents, chelants, anti corrosion agents, and teeth cleansing and whitening agents, and mixtures thereof.

VII. Product Forms

In one aspect, the consumer products disclosed herein may be personal care compositions. Such compositions can be applied to the skin and/or hair in order to provide cleansing and/or conditioning treatment. The compositions can be, for example, formulated as bars, liquids, emulsions, shampoos, gels, powders, sticks, hair conditioners (rinse off or leave in), hair tonics, pastes, hair colorants, sprays, mousses and other styling products.

In one aspect, the consumer products disclosed herein may be fabric and/or home care compositions. Such compositions can be applied to the fabrics, hard surfaces, ceramics, glass, wood, and the like in order to provide cleansing and/or conditioning treatment. The compositions can be formulated as bars, liquids, emulsions, gels, powders, sticks, pastes, sprays, mousses and the like.

Aspects of the invention include the use of the organosilicone polymers disclosed herein in laundry detergent compositions (e.g., TIDE™), hard surface cleaners (e.g., MR CLEAN™) automatic dishwashing liquids (e.g., CASCADE™), dishwashing liquids (e.g., DAWN™), and floor cleaners (e.g., SWIFFER™). Non-limiting examples of cleaning compositions may include those described in U.S. Pat. Nos. 4,515,705; 4,537,706; 4,537,707; 4,550,862; 4,561,998; 4,597,898; 4,968,451; 5,565,145; 5,929,022; 6,294,514; and 6,376,445.

The fabric or home care compositions disclosed herein are typically formulated such that, during use in aqueous cleaning operations, the wash water will have a pH of between 6.5 and 12, or between 7.5 and 10.5. Liquid dishwashing product formulations typically have a pH between 6.8 and 9.0. Cleaning products are typically formulated to have a pH of from 7 to 12. Techniques for controlling pH at recommended usage levels include the use of buffers, alkalis, acids, etc., and are well known to those skilled in the art.

VIII. Method of Making Compositions

Any suitable method of making the composition of the present invention may be used. In one embodiment, the pendant organopolysiloxane conditioning polymer is blended with the other ingredients present in the composition. In an alternate embodiment, the pendant organopolysiloxane of the present invention is pre-emulsified, optionally with other ingredients that do not adversely adsorb onto the pendant organopolysiloxane conditioning polymer, then blended with the other components of the finished composition, according to standard methods known in the art. The typical procedure for pre-emulsified embodiments involves pre-emulsifying the pendant organopolysiloxane conditioning agent with an aliquot of solvent (e.g., hydrophilic solvent such as water), then adding the balance of solvent and other materials that are being included in the final consumer product formulation.

It would be appreciated by one of ordinary skill in the art that any of a number of other methods might be used to make compositions comprising the organosiloxane polymer of the present invention. For example, it is not necessary to pre-emulsify the pendant organopolysiloxane conditioning polymer in a separate step but rather it may be emulsify at any point in the making process, as desired. Alternately, it may not be necessary to emulsify the organosiloxane polymer at all, depending upon whether the polymer is soluble in the composition's carrier. Alternately, if the carrier is a solid or semi-solid the organosiloxane conditioning polymer might be directly applied to the carrier.

Similarly, the compositions comprising the roganopolysiloxane conditioning polymer might include any of a number of ingredients including any of the non-limiting ingredients and/or ingredient types discussed herein. Details of the incorporation of said optional ingredients are known to one of skill in the art and the cleaning and/or treatment compositions of the present invention can be formulated into any suitable form and prepared by any process chosen by the formulator, non-limiting examples of which are described in U.S. Pat. No. 5,879,584; U.S. Pat. No. 5,691,297; U.S. Pat. No. 5,574,005; U.S. Pat. No. 5,569,645; U.S. Pat. No. 5,565,422; U.S. Pat. No. 5,516,448; U.S. Pat. No. 5,489,392; U.S. Pat. No. 5,486,303 all of which are incorporated herein by reference.

IX. Methods of Use

Certain of the consumer products disclosed herein can be used to clean or treat a substrates inter alia a substrate or fabric including physiological substrates and non-physiological substrates. Typically at least a portion of the substrates is contacted with an embodiment of Applicants' composition, in neat form or diluted in a liquor, for example, a wash liquor and then the substrates may be optionally washed and/or rinsed. In one aspect, a substrates is optionally washed and/or rinsed, contacted with a particle according to the present invention or composition comprising said particle and then optionally washed and/or rinsed. For purposes of the present invention, washing includes but is not limited to, scrubbing, and mechanical agitation. The fabric may comprise most any fabric capable of being laundered or treated in normal consumer use conditions. Liquors that may comprise the disclosed compositions may have a pH of from 3 to 11.5. Such compositions are typically employed at concentrations of from 500 ppm to 15,000 ppm in solution. When the wash solvent is water, the water temperature typically ranges from 5° C. to 90° C. and, when the substrates comprises a fabric, the water to fabric ratio is typically from 1:1 to 30:1.

EXAMPLES

The following examples further describe and demonstrate typical embodiments within the scope of the present invention. The examples are given solely for the purpose of illustration and are not to be construed as limitations of the present invention since many variations thereof are possible without departing from the spirit and scope of the invention. Ingredients are identified by chemical name, or otherwise defined below.

The samples in Table 1 are prepared according to the above instructions using the amounts shown.
Particle Made in the Presence of Non-Ionic Emulsifiers (2 Different HLB's)
(HLB=hydrophilic lipophilic balance)
Preparation of a $H_2O$/Silicone emulsion, using low HLB surfactant/emulsifier then invert during dilution to form Silicone/$H_2O$ emulsion.

| RM | Examples | Level (wt % of total composition) |
| --- | --- | --- |
| Silicone fluid | Amino Silicone or PDMS | 40% |
| Emulsifier #1 | Tergitol 15-s-5 | 1.25 |
| Deposition aid | Cationic pendant aminosilicone of the present invention | 1.8% |
| Emulsifier #2 | Tergitol 15-s-12 | 1.93 |
| Water | Distilled | To 100% |
| Acetic Acid | Glacial | to pH 5 |

Using IKA T25 Ultra-Turrax disperser (300 W Output) and IKA Dispersing element (S25N-25G), in a non-plastic container, add silicone fluid and polymer. Mix for 5 minutes at 500 RPM. Add Emulsifier #1, mix for 5 min at 500 RP. In a separate container, blend Emulsifier #2 and water, mix until completely dispersed. Add water+emulsifier #2 composition to Silicone/polymer/emulsifier #1 composition, in 3 equal aliquots. After addition of each aliquot, mix at 3,000 RPM until homogeneous and uniform consistency. After all of the water+emulsifier #2 is combined, add glacial acetic acid to adjust pH, mix for 20 minutes at 3,000 RPM.

Example 2: Non-Ionic Emulsifier (1 Non-Ionic Surfactant/Emulsifier)

Preparation Via Single Emulsifier Preparation Method

| RM | Examples | Level (wt % of total composition) |
|---|---|---|
| Water | Distilled | To 100% |
| Emulsifier #1 | Lutensol XP70 (BASF) | 5% |
| Silicone fluid | Amino Silicone or PDMS | 40% |
| Deposition aid | Cationic pendant aminosilicone of the present invention | 4% |
| Acetic Acid | Glacial | to pH 5 |

Using IKA T25 Ultra-Turrax disperser (300 W Output) and IKA Dispersing element (S25N-25G), in a non-plastic container, blend Emulsifier #1 and water, mix until completely dispersed. In a separate non-plastic container, fluid and polymer. Mix for 5 minutes at 500 RPM. Add Silicone polymer composition to the water/emulsifier #1 composition at approximately 10 gram/min, with constant mixing at 3,000 RPM. Mix entire composition for 20 minutes at 3,000 RPM. Add glacial acetic acid to adjust pH, mix for 3 minutes at 3,000 RPM.

Example 3: Polymer Emulsifier (No Added Surfactant/Emulsifier)

Preparation Via Single Emulsifier Using Polymer Emulsifier Preparation Method

| RM | Examples | Level (wt % of total composition) |
|---|---|---|
| Deposition aid | Cationic pendant aminopolysiloxane of the present invention | 2.25% |
| Water | Distilled | To 100% |
| Silicone fluid | Amino Silicone or PDMS | 40% |
| Acetic Acid | Glacial | to pH 5 |

Follow preparation method in Example #2 except add polymer to water and no addition to silicone fluid.

Example: Heavy Duty Liquid Detergents

The following heaving duty liquid detergents are made by mixing the ingredients listed below via conventional processes. Such heavy duty liquid detergents are used to launder fabrics that are then dried by line drying and/or machine drying. Such fabrics may be treated with a fabric enhancer prior to and/or during drying. Such fabrics exhibit a clean appearance and have a soft feel.

| Ingredient | Example I Wt % | Example II Wt % | Example III Wt % | Example IV Wt % | Example V Wt % | Example VI Wt % |
|---|---|---|---|---|---|---|
| C12-15 alkyl polyethoxylate (1.8) sulfate[1] | 16.0 | 16.0 | 14.6 | 8.0 | 20.1 | 7.3 |
| C12 alkyl trimethyl ammonium chloride[2] | — | — | — | — | 2.0 | — |
| C16/C17 Sodium Alkylsulfonate (HSAS)[3] | 1.9 | 1.9 | 1.7 | — | — | 0.85 |
| Sodium alkylbenzenesulfonate[3] | 4.5 | 4.9 | 4.4 | 3.5 | — | 2.0 |
| 1,2 Propane diol/diethylene glycol | 4.7 | 4.8 | 4.4 | 2.6 | 4.9 | 2.7 |
| Ethanol | 1.9 | 1.9 | 1.9 | 1.1 | 2.7 | 0.9 |
| Neodol 23-9[9] | 0.7 | 0.7 | 0.7 | 0.3 | 0.8 | 0.4 |
| $C_{12-18}$ Fatty Acid[4] | 1.6 | 1.6 | 1.4 | 0.5 | 1.0 | 0.7 |
| Citric acid | 3.6 | 3.6 | 3.3 | 1.5 | 3.4 | 1.6 |
| Enzymes, (Protease[5], amylase[5]) | 1.8 | 1.8 | 1.6 | 0.6 | 0.35 | 0.8 |
| Fluorescent Whitening Agent[6] | 0.21 | 0.19 | 0.19 | 0.07 | 0.08 | 0.13 |
| DTPA | 0.35 | 0.32 | 0.32 | 0.4 | 0.5 | 0.2 |
| Ethoxylated polyamine[7] | 2.5 | 1.6 | 1.6 | 1.5 | 0.6 | 0.75 |
| Hydrogenated castor oil | — | 0.12 | 0.12 | 0.6 | 0.12 | 0.1 |
| Ethoxylated hexamethylane diamine[8] | 1.5 | — | — | — | — | — |
| Particle according to present invention comprising Silicone[9] and pendant cationic aminosilicone in ratio of (20:1) | 1.56 | 3.15 | 5.25 | 5.25 | 4.2 | 5.25 |
| Water and adjuncts[11] | Balance to 100% | | | | | |

[1]Available from Shell Chemicals, Houston, TX
[2]Available from Degussa Corporation, Hopewell, VA.
[3]Available from Shell Chemicals, Houston, TX.
[4]Available from The Procter & Gamble Company, Cincinnati, OH.
[5]Available from Genencor International, South San Francisco, CA.
[6]Available from Ciba Specialty Chemicals, High Point, NC.
[7]Sold under the tradename LUTENSIT ®, available from BASF (Ludwigshafen, Germany) and described in WO 01/05874.
[8]Available from Nippon Shokkabai
[9]Aminofunctional silicones,; KF869, KF867 Shin-Etsu Silicones, Tokyo, Japan; a polydimethyl siloxane of viscosity 5000, 10000 Cst available from Gilest, Morrisville, PA, USA and 60,000 centistroke available from Dow Corning Corporation, Midland, MI.
[11]May include, but not limited to: stabilizers, perfumes, dyes, rheology modifiers, opacifier, cleaning polymers Example: Heavy Duty Liquid Detergent

| Ingredient | Example VII Wt % | Example VIII Wt % | Example IX Wt % | Example X Wt % | Example XI Wt % | Example XII Wt % |
|---|---|---|---|---|---|---|
| C12-15 alkyl polyethoxylate (1.8) sulfate[1] | 16.0 | 16.0 | 14.6 | 8.0 | 20.1 | 7.3 |
| C12 alkyl trimethyl ammonium chloride[2] | — | — | — | — | 2.0 | — |
| C16/C17 Sodium Alkylsulfonate (HSAS)[3] | 1.9 | 1.9 | 1.7 | — | — | 0.85 |
| Sodium alkylbenzenesulfonate[4] | 4.5 | 4.9 | 4.4 | 3.5 | — | 2.0 |
| 1,2 Propane diol/diethylene glycol | 4.7 | 4.8 | 4.4 | 2.6 | 4.9 | 2.7 |
| Ethanol | 1.9 | 1.9 | 1.9 | 1.1 | 2.7 | 0.9 |
| Neodol 23-9[9] | 0.7 | 0.7 | 0.7 | 0.3 | 0.8 | 0.4 |
| $C_{12-18}$ Fatty Acid[5] | 1.6 | 1.6 | 1.4 | 0.5 | 1.0 | 0.7 |
| Citric acid | 3.6 | 3.6 | 3.3 | 1.5 | 3.4 | 1.6 |
| Enzymes, (Protease[5], amylase[5]) | 1.8 | 1.8 | 1.6 | 0.6 | 0.35 | 0.8 |
| Fluorescent Whitening Agent | 0.21 | 0.19 | 0.19 | 0.07 | 0.08 | 0.13 |
| DTPA | 0.35 | 0.32 | 0.32 | 0.4 | 0.5 | 0.2 |
| Ethoxylated polyamine[7] | 2.5 | 1.6 | 1.6 | 1.5 | 0.6 | 0.75 |
| Hydrogenated castor oil | — | 0.12 | 0.12 | 0.6 | 0.12 | 0.1 |
| Ethoxylated hexamethylane diamine[8] | 1.5 | — | — | — | — | — |
| Silicone[9] | — | 3.0 | | 5.0 | 1.0 | |
| Cationic pendant aminosilicone | 0.3 | 0.2 | 0.5 | 0.2 | 0.15 | 5.0 |
| Water and adjuncts[10] | | Balance to 100% | | | | |

[1]Available from Shell Chemicals, Houston, TX
[2]Available from Degussa Corporation, Hopewell, VA.
[3]Available from Shell Chemicals, Houston, TX.
[4]Available from The Procter & Gamble Company, Cincinnati, OH.
[5]Available from Genencor International, South San Francisco, CA.
[6]Available from Ciba Specialty Chemicals, High Point, NC.
[7]Sold under the tradename LUTENSIT ®, available from BASF (Ludwigshafen, Germany) and described in WO 01/05874.
[8]Available from Nippon Shokkabai
[9]Aminofunctional silicones,; KF869, KF867 Shin-Etsu Silicones, Tokyo, Japan; a polydimethyl siloxane of viscosity 5000, 10000 Cst available from Gilest, Morrisville, PA, USA and 60,000 centistroke available from Dow Corning Corporation, Midland, MI.
[10] May include, but not limited to: stabilizers, perfumes, dyes, rheology modifiers, opacifier, cleaning polymers Example: Hair Conditioners The following are non-limiting examples of hair conditioning compositions of the present invention made by one or more of the processes of making disclosed in the present specification.

| Ingredient | EXAMPLE COMPOSITION | | | | | |
|---|---|---|---|---|---|---|
| | I | II | III | IV | V | VI |
| Water | q.s. to 100% | q.s. to 100% | q.s. to 100% | q.s. to 100% | q.s. to 100% | q.s. to 100% |
| Particle according to present invention comprising Silicone [1] and cationic pendant aminosilicone from in ratio of (20:1) | 5.00 | 5.00 | 5.00 | 3.00 | 2.00 | 1.00 |
| Behentrimonium methosulfate/IP [3] | 2.37 | 3.45 | — | — | — | — |
| Stearamidopropyl Dimethylamine[4] | — | — | 1.19 | 1.19 | 1.19 | 1.19 |
| Cetyl alcohol [5] | 1.15 | 1.07 | 1.73 | 1.73 | 1.73 | 1.73 |
| Stearyl alcohol [6] | 2.88 | 2.66 | 3.19 | 3.19 | 3.19 | 3.19 |
| Disodium EDTA | 0.13 | 0.13 | 0.14 | 0.14 | 0.14 | 0.14 |
| Benzyl alcohol | 0.41 | 0.40 | 0.45 | 0.45 | 0.45 | 0.45 |
| Methylchloroisothiazolinone/ Methylisothiazolinone [7] | 0.03 | 0.03 | 0.04 | 0.04 | 0.04 | 0.04 |
| Panthenol [8] | — | 0.05 | — | — | — | — |
| Panthenyl ethyl ether [9] | — | 0.03 | — | — | — | — |
| Fragrance | 0.51 | 0.50 | — | — | — | — |
| Dicetyldimonium | — | — | 0.57 | 0.57 | 0.57 | 0.57 |

-continued

| Ingredient | EXAMPLE COMPOSITION | | | | | |
| --- | --- | --- | --- | --- | --- | --- |
| | I | II | III | IV | V | VI |
| Chloride in Propylene Glycol | | | | | | |
| L-Gutamic Acid | — | — | 0.38 | 0.38 | 0.38 | 0.38 |
| Citric Acid Anhydrous | — | — | 0.06 | 0.06 | 0.06 | 0.06 |

[1] Aminofunctional silicones,; KF869, KF867 Shin-Etsu Silicones, Akron OH; CF42-xxx from Momentive Silicones, Akron, OH, USA; a polydimethyl siloxane of viscosity 5000, 10000 Cst available from Gilest, Morrisville, PA, USA and 350, 5000, 60,000 centistroke available from Dow Corning Corporation, Midland, MI.
[3] Behentrimonium methosulfate/Isopropyl alcohol: Genamin BTMS available from Clariant
[4] Stearamidopropyl Dimethylamine
[5] Cetyl alcohol: Konol TM series available from Shin Nihon Rika
[6] Stearyl alcohol: Konol TM series available from Shin Nihon Rika
[7] Methylchloroisothiazolinone/Methylisothiazolinone: Kathon TM CG available from Rohm & Haas
[8] Panthenol: Available from Roche
[9] Panthenyl ethyl ether: Available from Roche Analytical Methods Assessing Silicone Deposition.

Swatches of hair are treated with hair conditioners of the present invention containing the benefit agent emulsion of the present invention during the rinse cycle. After completion of the rinse, hair swatches are dried in air at room temperature; the hair swatches are cut into smaller pieces and are analyzed for the amount of silicone deposited per gram of hair. The extraction solvent is selected. For nonpolar silicones, the extraction solvent is toluene/Methyl isobutyl ketone (50%//50%). For polar silicones, the extraction is Methyl isobutyl ketone/methanol/AE3S (84.45%/15.5%/0.05%). The amount of silicone deposited is determined by the ICP/MS.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A benefit agent emulsion comprising a benefit agent and a pendant organopolysiloxane having the formula:

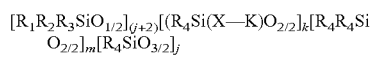

wherein:

j is an integer from 0 to about 98;

k is an integer from 1 to about 200;

m is an integer from 4 to about 5,000;

$R^1$, $R^2$ and $R^3$ are each independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy, $C_1$-$C_{32}$ substituted alkoxy and X—K;

each $R_4$ is independently selected from the group consisting of H, OH, $C_1$-$C_{32}$ alkyl, $C_1$-$C_{32}$ substituted alkyl, $C_5$-$C_{32}$ or $C_6$-$C_{32}$ aryl, $C_5$-$C_{32}$ or $C_6$-$C_{32}$ substituted aryl, $C_6$-$C_{32}$ alkylaryl, $C_6$-$C_{32}$ substituted alkylaryl, $C_1$-$C_{32}$ alkoxy and $C_1$-$C_{32}$ substituted alkoxy;

for each X—K, X comprises a divalent alkylene radical comprising 2-12 carbon atoms, each divalent alkylene radical is independently selected from the group consisting of —$(CH_2)_s$— wherein s is an integer from 2 to 8; and each K is selected independently from the group consisting

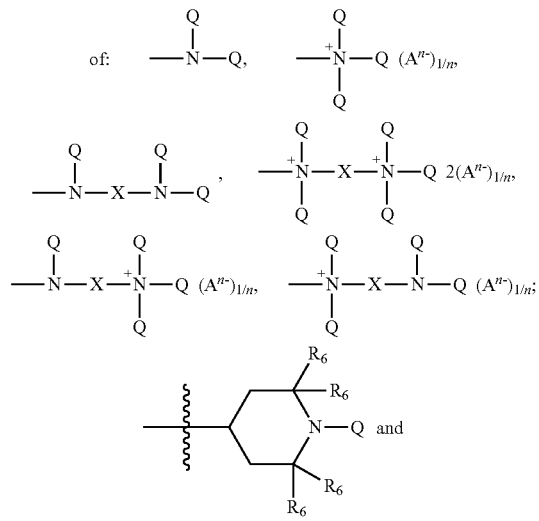

-continued

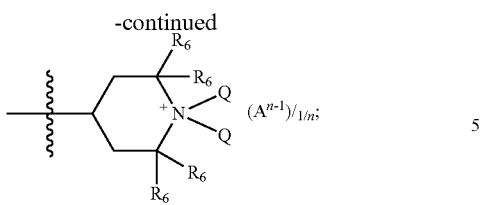

each Q is independently a H or a $C_1$-$C_{32}$, linear or branched, substituted or unsubstituted hydrocarbon, with the proviso that when K is a quat, Q cannot be an amide, imine, or urea moiety and if Q is an amide, imine, or urea moiety, then any additional Q bonded to the same nitrogen as said amide, imine, or urea moiety must be H or a $C_1$-$C_6$ alkyl;

X is defined as above;

for K $A^{n-}$ is a suitable charge balancing anion;

wherein the pendant organopolysiloxane and the benefit agent are different relative to each other, wherein the pendant organopolysiloxane is adsorbed onto the benefit agent; and wherein the benefit agent is a silicone selected from the group consisting of a polydimethylsiloxane, an aminosilicone, a cationic silicone, a silicone polyether, a cyclic silicone, a silicone resin, a fluorinated silicone, and mixtures thereof wherein the pendant organopolysiloxane has a molecular weight of from about 15,000 to about 50,000 Daltons, where the ratio of benefit agent to organopolysiloxane is from 1000:1 to 1:1, by weight and wherein the benefit agent is physically blended with pendant organopolysiloxane before addition to other ingredients.

* * * * *